US010633643B2

(12) United States Patent
Pavlik et al.

(10) Patent No.: US 10,633,643 B2
(45) Date of Patent: Apr. 28, 2020

(54) ENGINEERED *CLOSTRIDIUM BOTULINUM* TOXIN ADAPTED TO DELIVER MOLECULES INTO SELECTED CELLS

(71) Applicant: Board of Regents of the University of Nebraska, Lincoln, NE (US)

(72) Inventors: Benjamin J. Pavlik, Lincoln, NE (US); Paul Blum, Lincoln, NE (US); Kevin Van Cott, Hickman, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 0 days.

(21) Appl. No.: 15/574,151

(22) PCT Filed: May 14, 2016

(86) PCT No.: PCT/US2016/032573
§ 371 (c)(1),
(2) Date: Nov. 14, 2017

(87) PCT Pub. No.: WO2016/187076
PCT Pub. Date: Nov. 24, 2016

(65) Prior Publication Data
US 2018/0127734 A1 May 10, 2018

Related U.S. Application Data

(60) Provisional application No. 62/162,582, filed on May 15, 2015.

(51) Int. Cl.
| C12N 9/52 | (2006.01) |
| A61K 47/64 | (2017.01) |
| A61K 38/45 | (2006.01) |
| A61K 49/00 | (2006.01) |
| C07K 14/33 | (2006.01) |
| C12N 15/62 | (2006.01) |

(52) U.S. Cl.
CPC ............ *C12N 9/52* (2013.01); *A61K 38/45* (2013.01); *A61K 47/6415* (2017.08); *A61K 49/0056* (2013.01); *C07K 14/33* (2013.01); *C12N 15/62* (2013.01); *C12Y 204/02* (2013.01); *C12Y 304/24069* (2013.01); *C07K 2319/33* (2013.01); *Y02A 50/469* (2018.01)

(58) Field of Classification Search
None
See application file for complete search history.

(56) References Cited

U.S. PATENT DOCUMENTS

2004/0208889 A1* 10/2004 Sutton ............... A61K 47/65
424/190.1
2006/0110409 A1 5/2006 Shone et al.
2009/0269361 A1 10/2009 Shone et al.
2013/0288374 A1 10/2013 Oyler et al.
2015/0044210 A1* 2/2015 Mechaly ............... C07K 16/32
424/134.1

FOREIGN PATENT DOCUMENTS

EP 1452589 A1 9/2004
WO WO 2013/126690 8/2013

OTHER PUBLICATIONS

Chen et al. Adv Drug Deliv Rev. Oct. 15, 2013: 65(10):1357-1369.*
Deng et al. Annu. Rev. Microbiol. 2008. 62:271-88.*
Kaiser et al. Biochemistry 2006, 45, 13361-13368.*
Uniprot Accession # Q332E0 Dec. 6, 2005.*
Uniprot Accession D4N871 May 18, 2010.*
Uniprot Accession # O86171 Nov. 1998.*
Goodnough et al. FEBS Letters 513 (2002) 163-168.*
Schiavo, G., Matteoli, M. & Montecucco, C. "Neurotoxins affecting neuroexocytosis." Physiol. Rev. 80, 717-766 (2000).
Singh, B. R. et al. "Clostridial neurotoxins as a drug delivery vehicle targeting nervous system." Biochimie 92, 1252-1259 (2010).
Vazquez-Cintron, E. J. et al. "A toxic derivative of botulinum neurotoxin A as a prototype molecular vehicle for targeted delivery to the neuronal cytoplasm." PLoS One 9, doi: e8551710.1371/journal.pone.0085517 (2014).
Zhang, P. et al. "An efficient drug delivery vehicle for botulism countermeasure." BMC Pharmacal. 9, doi: 10.1186/1471-2210-9-12 (2009).
Ho, M. F. et al. "Recombinant botulinum neurotoxin A heavy chain-based delivery vehicles for neuronal cell targeting." Protein Eng. Des. Sel. 24, 247-253 (2011).
Webb, R. P., Smith, T. J., Wright, P., Brown, J. & Smith, L.A. "Production of catalytically inactive BoNT/A1 holoprotein and comparison with BoNT/A1 subunit vaccines against toxin subtypes A1, A2, and A3." Vaccine 27, 4490-4497 (2009).
Mechaly, A., McCluskey, A. J. & Collier, R. J. "Changing the receptor specificity of anthrax toxin." mBio 3, e00088-00012, doi: 10.1128/ mBio.00088-12 (2012).
Fahrer, J. et al. "C2-streptavidin mediates the delivery of biotin-conjugated tumor suppressor protein P53 into tumor cells." Bioconjug. Chem. 24, 595-603 (2013).
Fahrer, J., Rieger, J., van Zandbergen, G. & Barth, H. "The C2-streptavidin delivery system promotes the uptake of biotinylated molecules in macrophages and T-leukemia cells." Biol. Chem. 391, 1315-1325 (2010).

(Continued)

*Primary Examiner* — Oluwatosin A Ogunbiyi
(74) *Attorney, Agent, or Firm* — Lathrop GPM LLP

(57) ABSTRACT

An engineered payload-delivery system includes a target cell binding unit, covalently bound to a pore forming unit, and a payload portion adapted with a region capable of non-covalently binding to the pore forming unit. The pore forming unit is derived from a particular sub-serotype of *Clostridium* toxin, while the payload region is derived from a different sub-serotype of *Clostridium* toxin. The disclosed chimeric protein-based composition is capable of specifically delivering payload to neural cells.

17 Claims, 5 Drawing Sheets

Specification includes a Sequence Listing.

(56) References Cited

OTHER PUBLICATIONS

Fahrer, J. et al. "Genetically engineered clostridial C2 toxin as a novel delivery system for living mammalian cells." Bioconjug. Chem. 21, 130-139 (2010).
Schleberger, C., Hochmann, H., Barth, H., Aktories, K. & Schulz, G. E. "Structure and action of the binary C2 toxin from Clostridium botulinum." J. Mol. Biol. 364, 705-715 (2006).
Aktories, K. et al. "Botulinum-C2 toxin ADP-ribosylates actin." Nature 322, 390-392 (1986).
Simpson, L. L. "Molecular basis for the pharmacological actions of Clostridium botulinum type C2 toxin." J. Pharmacol. Exp. Ther. 230, 665-669 (1984).
Ohishi, I., Iwasaki, M. & Sakaguchi, G. "Purification and characterization of 2 components of botulinum C2 toxin." Infect. Immun. 30, 668-673 (1980).
Iwasaki, M., Ohishi, I. & Sakaguchi, G. "Evidence that botulinum C2-toxin has 2 dissimilar components." Infect. Immun. 29, 390-394 (1980).
Ohishi, I. "Activation of botulinum C2 toxin by trypsin." Infect. Immun. 55, 1461-1465 (1987).
Nagahama, M. et al. "Binding and Internalization of Clostridium botulinum C2 Toxin." Infect. Immun. 77, 5139-5148 (2009).
Fritz, G., Schroeder, P. & Aktories, K. "Isolation and characterization of a Clostridium botulinum C2 toxin-resistant cell line: evidence for possible involvement of the cellular C2II receptor in growth-regulation." Infect. Immun. 63, 2334-2340 (1995).
Pust, S., Barth, H. & Sandvig, K. "Clostridium botulinum C2 toxin is internalized by clathrin- and Rho-dependent mechanisms." Cell Microbiol. 12, 1809-1820 (2010).
Kaiser, E., Haug, G., Hliscs, M., Aktories, K. & Barth, H. "Formation of a biologically active toxin complex of the binary Clostridium botulinum C2 toxin without cell membrane interaction." Biochemistry 45, 13361-13368 (2006).
Barth, H. et al. "Cellular uptake of Clostridium botulinum C2 toxin requires oligomerization and acidification." J. Biol. Chem. 275, 18704-18711 (2000).
Haug, G. et al. "Cellular uptake of Clostridium botulinum C2 toxin: Membrane translocation of a fusion toxin requires unfolding of its dihydrofolate reductase domain." Biochemistry 42, 15284-15291 (2003).
Chaddock, J. A. et al. "Inhibition of vesicular secretion in both neuronal and nonneuronal cells by a retargeted endopeptidase derivative of Clostridium botulinum neurotoxin type A." Infect. Immun. 68, 2587-2593 (2000).
Blocker, D. et al. "The C terminus of component C2II of Clostridium botulinum C2 toxin is essential for receptor binding." Infect. Immun. 68, 4566-4573 (2000).
Gill, D. M. "Bacterial toxins-a table of lethal amounts." Microbiol. Rev. 46, 86-94 (1982).
Montecucco, C. & Schiavo, G. "Mechanism of action of tetanus and botulinum neurotoxins." Mol. Microbiol. 13, 1-8 (1994).
Strotmeier, J. et al. "The biological activity of botulinum neurotoxin type C is dependent upon novel types of ganglioside binding sites." Mol. Microbial. 81, 143-156 (2011).
Simpson, L. L. "The origin, structure, and pharmacological activity of botulinum toxin." Pharmacal. Rev. 33, 155-188 (1981).
Yowler, B. C. & Schengrund, C. L. "Glycosphingolipids—Sweets for botulinum neurotoxin." Glycoconj. J. 21, 287-293 (2004).
Karalewitz, A. P. A., Fu, Z. J., Baldwin, M. R., Kim, J. J.P. & Barbieri, J. T. "Botulinum neurotoxin serotype C associates with dual ganglioside receptors to facilitate cell entry." J. Biol. Chem. 287,40806-40816 (2012).
Barth, H., Klingler, M., Aktories, K. & Kinzel, V. "Clostridium botulinum C2 toxin delays entry into mitosis and activation of p34(cdc2) kinase and cdc25-C phosphatase in HeLa cells." Infect. Immun. 67, 5083-5090 (1999).
Varkouhi, A. K., Scholte, M., Storm, G. & Haisma, H. J. "Endosomal escape pathways for delivery of biologicals." J. Control. Release 151, 220-228 (2011).
Sandvig, K. & van Deurs, B. "Delivery into cells: lessons learned from plant and bacterial toxins." Gene Ther. 12, 865-872 (2005).
Verdurmen, W. P., Luginbuhl, M., Honegger, A. & Pluckthun, a. "Efficient cell specific uptake of binding proteins into the cytoplasm through engineered modular transport systems." J. Control. Release 200, 13-22 (2015).
Eckhardt, M., Barth, H., Blocker, D. & Aktories, K. "Binding of Clostridium botulinum C2 toxin to asparagine-linked complex and hybrid carbohydrates." J. Biol. Chem. 275, 2328-2334 (2000).
Andreu, A., Fairweather, N. & Miller, A. D. "Clostridium neurotoxin fragments as potential targeting moieties for liposomal gene delivery to the CNS." ChemBioChem 9, 219-231 (2008).
Edupuganti, 0. P. et al. "Targeted delivery into motor nerve terminals of inhibitors for SNARE-cleaving proteases via liposomes coupled to an atoxic botulinum neurotoxin." FEBS J. 279, 2555-2567 (2012).
Tsukamoto, K. et al. "Binding of Clostridium botulinum type C and D neurotoxins to ganglioside and phospholipid-Novel insights into the receptor for clostridial neurotoxins." J. Biol. Chem. 280, 35164-35171 (2005).
Rummel, A. et al. "Botulinum neurotoxins C, E and F bind gangliosides via a binding site prior to stimulation-dependent uptake with botulinum neurotoxin F utilising the three isoforms of SV2 as second receptor." J. Neurochem. 110, 1942-1954 (2009).
Muraro, L., Tosatto, S., Motterlini, L., Rossetto, 0. & Montecucco, C. "The N-terminal half of the receptor domain of botulinum neurotoxin A binds to microdomains of the plasma membrane." Biochem. Biophys. Res. Commun. 380, 76-80 (2009).
Harper, C. B. et al. "Dynamin inhibition blocks botulinum neurotoxin type A endocytosis in neurons and delays botulism." J. Biol. Chem. 286, 35966-35976 (2011).
Couesnon, A., Pereira, Y. & Popoff, M. R. "Receptor-mediated transcytosis of botulinum neurotoxin A through intestinal cell monolayers." Cell Microbial. 10, 375-387 10 (2008).
Simpson, L. L. "Identification of the major steps in botulinum toxin action." Annu. Rev. Pharmacal. Toxicol. 44, 167-193 (2004).
Zhao, H. L. et al. "Increasing the homogeneity, stability and activity of human serum albumin and interferon-alpha 2b fusion protein by linker engineering." Protein Expr. Purif. 61, 15 73-77 (2008).
Bhandari, D. G., Levine, B. A., Trayer, I. P. & Yeadon, M. E. "H-1-NMR study of mobility and conformational constraints within the proline-rich N-terminal of the LC1 alkali light chain of skeletal myosin. Correlation with similar segments in other protein systems." Eur. J. Biochem. 160, 349-356 (1986).
Evans, J. S., Levine, B. A., Trayer, I. P., Donnan, C. J. & Higgins, C. F. "Sequenced-imposed structural constraints in the tonB protein of *Escherichia coli*." FEBS Lett. 208, 211-216 (1986).
Roditi, I. et al. "Expression of Trypanosoma brucei procyclin as a fusion protein in *Escherichia coli*." Mol. Biochem. Parasitol. 34, 35-43 (1989).
Kroken, A R. et al. "Unique Ganglioside Binding by Botulinum Neurotoxins C and DSA." FEBS J. 278,4486-4496 (2011).
Heine, K., Pust, S., Enzenmtiller, S. & Barth, H. "ADP-Ribosylation of Actin by the Clostridium botulinum C2 Toxin in Mammalian Cells Results in Delayed Caspase-Dependent Apoptotic Cell Death." Infect. Immun. 76, 4600-4608 (2008).
Barth, H., Roebling, R., Fritz, M. & Aktories, M. "The binary Clostridium botulinum C2 toxin as a protein delivery system—Identification of the minimal protein region necessary for interaction of toxin components." J. Biol. Chem. 277, 5074-5081 (2002).
Rabideau, A E., Liao, X., Ak9ay, G. & Pentelute, B. L. "Translocation of Non-Canonical Polypeptides into Cells Using Protective Antigen." Sci. Rep. 5, 11944 (2015).
Laemmli, U. K. "Cleavage of structural proteins during the assembly of the head of bacteriophage T4." Nature 227, 680-685 (1970).
Towbin, H., Staehelin, T. & Gordon, J. "Electrophoretic transfer of proteins from polyacrylamide gels to nitrocellulose sheets: procedure and some applications." PNAS 76, 5 4350-4354 (1979).
Burnette, W. N. "Western blotting-electrophoretic transfer of proteins from sodium dodecyl sulfate polyacrylamide gels to unmodified nitrocellulose and radiographic detection with antibody and radioiodinated protein-A." AnaL Biochem. 112, 195-203 (1981).

(56) References Cited

OTHER PUBLICATIONS

Ma, H. T. & Poon, R. Y. "Synchronization of HeLa cells." Methods Mol. Bioi. 761, 10 151-161 (2011).

Barth, H., Preiss, J. C., Hofmann, F. & Aktories, K. "Characterization of the catalytic site of the ADP-ribosyltransferase Clostridium botulinum C2 toxin by site-directed mutagenesis." J. Bioi. Chern. 273, 29506-29511 (1998).

Barth et al. (2002) "The uptake machinery of clostridial actin ADP-ribosylating toxins: A cell delivery system for fusion proteins and polypeptide drugs," Naunyn-Schmiedeberg's Archives of Pharmacology, vol. 366, No. 6, pp. 501-512.

Zou et al. (2012) "Construction of a cellulase hyper-expression system in Trichoderma reesei by promoter and enzyme engineering," Microbial Cell Factories, vol. 11, No. 1, p. 21.

European Patent Application No. 16797057.3, Extended Search and Opinion dated Mar. 1, 2019, 14 pages.

\* cited by examiner

ENGINEERED *CLOSTRIDIUM BOTULINUM* TOXIN ADAPTED TO DELIVER MOLECULES INTO SELECTED CELLS

RELATED APPLICATION

This application claims priority to U.S. Provisional Patent Application No. 62/162,582, filed May 15, 2015, which is incorporated by reference into the present application in its entirety and for all purposes.

GOVERNMENT RIGHTS

This invention was made with government support under grant number HDTRA-10-C-0055 awarded by Defense Threat Reduction Agency of the Department of Defense. The government has certain rights in the invention.

BACKGROUND

*Clostridium botulinum*, a spore-forming, heat-resistant, anaerobic bacterium, produces a protein-based toxin (botulinum toxin) having several serotypes, known as A through G serotypes, of which serotype C has 3 subtypes, known as serotypes C1, C2 and C3. The C1 neurotoxin paralyzes people and animals in low doses by blocking acetylcholine release by neurons, recovery is slow-treatment may require ventilation for multiple weeks before a person is able to breathe again. The C2 toxin is not a neuro-active, and causes necrosis and hemorrhaging. The C3 toxin is the least characterized of the C sub-serotypes.

Most toxin-based delivery systems are multi-domain proteins that bind target cells and translocate material (payloads) across the lipid bilayer into the cytosol of the targeted cell. These systems are altered AB-type toxins, consisting of a payload domain (A) and a binding/translocation domain (B). The A and B domains can be covalently linked by a polypeptide or disulfide bond that is later cleaved during the translocation step. Non-covalently linked (binary) A and B toxin domains are transcribed and translated independently and associate prior to exerting toxicity. The *Clostridium botulinum* C2 toxin (C2) is not a neurotoxin, but it has a binary AB toxin design.

SUMMARY

The present disclosure advances the art by providing chimeric toxin-based delivery compositions (or systems) for delivering payload (or agent) to a target cell. In one embodiment, the composition may contain a target cell binding unit, a pore-forming unit and a payload unit, with or without other additional components.

In one embodiment, the pore-forming unit may be the same as the pore-forming unit of known toxins, for example, toxins from *Clostridium botulinum*. In another embodiment, the pore-forming unit may be derived from the pore-forming unit of known toxins with modifications. In another embodiment, the pore-forming unit may be any proteins that may function as a pore-forming unit.

The payload unit may contain the agent to be delivered to the target cell. In one aspect, the payload unit may bind non-covalently to the pore forming unit, or to the linked pore forming unit and target cell binding unit. In another aspect, the pore forming unit and target cell binding unit are linked covalently.

In one embodiment, the payload unit may be the same as the payload unit of known toxins, for example, toxins from *Clostridium botulinum*. In another embodiment, the payload unit may be derived from the payload unit of known toxins with modifications. In another embodiment, the payload unit may be any proteins that may function as a payload unit for the delivery of the agent.

In another embodiment, the target cell binding unit may contain a specific target cell binding ligand selected from the group consisting of antibody, antibody fragment, affibody, growth factor, a receptor-binding ligand, or combinations thereof. In another embodiment, the target cell binding unit may contain a native or modified binding domain derived from a heavy chain of *C. botulinum* toxin other than C2.

In another embodiment, the target cell binding unit preferentially binds to a neural cell. In another embodiment, the composition preferentially delivers the agent to neural cells. In another embodiment, the target cell binding unit is the binding domain of the heavy chain of *C. botulinum* neurotoxin C1 (C1 Hcc) (See FIG. 2c, corresponding to amino acids 230-426 of SEQ ID NO: 1).

In another embodiment, the pore-forming unit may be a polypeptide derived from a first type of non-neurotoxic (i.e., not specifically targeting neuron) toxin, and the target cell binding unit may be a polypeptide derived from a second type of toxin, wherein the second type is different from the first type of toxin. In another embodiment, the first type of non-neurotoxic toxin may be a binary toxin.

In another embodiment, the pore-forming unit may be a polypeptide derived from a first *Clostridium* toxin sub-serotype, while the target cell binding unit is a polypeptide derived from a second *Clostridium* toxin sub-serotype, wherein the second sub-serotype is different from the first sub-serotype. In another embodiment, the pore-forming unit is a polypeptide derived from the pore-forming unit of *Clostridium botulinum* toxin C2 (See FIG. 2c, corresponding to amino acids 1-591 of SEQ ID NO: 2).

In another embodiment, the pore-forming unit may contain a native or modified domain derived from a toxin other than *C. botulinum* toxin C2. In one aspect, the pore-forming unit may contain a native or modified pore-forming domain derived from a toxin selected from the group consisting of *Clostridium perfringens* alpha-, beta-, epsilon- and iota-toxin, *Clostridium spiroforme* Iota-like toxin, anthrax toxin, and combinations thereof.

In one embodiment, the pore-forming unit is a polypeptide derived from the pore-forming unit of *Clostridium botulinum* toxin C2, while the target cell binding unit may contain a native or modified binding domain derived from a toxin other than *C. botulinum* toxin C2. In one aspect, the target cell binding unit may contain a native or modified binding domain derived from a toxin selected from the group consisting of *C. botulinum* neurotoxins, *Clostridium perfringens* toxins alpha, beta, epsilon and iota toxin, *Clostridium spiroforme* Iota-like toxin, cholera toxin, anthrax toxin, shiga toxin, shiga-like toxin, diphtheria toxin, ricin, exotoxin A, and combinations thereof.

In another embodiment, the payload unit is not covalently bound to the target cell binding unit or the pore-forming unit. In another embodiment, the payload unit is a polypeptide derived from *Clostridium botulinum* toxin C2 (See FIG. 2d, SEQ ID NO: 3).

In another embodiment, the agent comprises at least one member selected from the group consisting of a therapeutic agent, a diagnostic agent, an imaging agent, and combinations thereof. In another aspect, the agent may contain at least one member selected from the group consisting of a toxin, a cell cycle blocker, an apoptosis inducing agent, an inhibitor of DNA replication, an inhibitor of RNA synthesis, an inhibitor of protein synthesis, an enzyme, a protein binding agent, an antibody, a neutralizing antibody, a labeling agent, magnetic beads, and combinations thereof.

In another embodiment, the agent comprises an ADP-ribosyltransferase. In another embodiment, the agent comprises C2I from *Clostridium botulinum* toxin C-2. In another embodiment, the agent comprises a fluorescent agent for labeling or monitoring the target cell.

In one embodiment, the target cell may be a cancer cell. In another embodiment, the target cell may be a neuron. In another embodiment, the target cell may be a cell of a brain tumor, a cell of a neuroblastoma, a cell of a retinoblastoma, a peripheral neuron, a motor neuron, a sensory neuron, or combinations thereof.

In another embodiment, the engineered payload-delivery composition may include a target-cell binding unit that is covalently bound to a pore-forming unit, and a payload portion adapted with a region capable of non-covalently binding to the pore forming unit. In another embodiment, a polypeptide (SEQ ID NO: 4) is disclosed which may contain the target-cell binding unit covalently bound to the pore-forming unit linked by a linker, $(EP)_{10}$, wherein the target-cell binding unit is the binding domain of the heavy chain of *C. botulinum* neurotoxin C1 (C1 Hcc) and the pore-forming unit is a polypeptide derived from the pore-forming unit of *Clostridium botulinum* toxin C2.

In another embodiment, the active payload region is bound to the pore-forming unit through a coupling region derived from the light-chain payload portion of botulinum toxin C-2. In another aspect, the target-cell binding unit is derived from the target-cell binding unit of botulinum toxin C-1.

In another embodiment, the target cell binding unit is the binding domain from the heavy chain of *C. botulinum* neurotoxin C1 (C1 Hcc), while the pore-forming unit is the pore-forming unit of *Clostridium botulinum* toxin C-2, and the payload unit comprises C2I from *Clostridium botulinum* toxin C-2.

In another embodiment, in a composition for delivering an agent to a target cell comprising a target cell binding unit, a pore-forming unit and a payload unit, the target cell binding unit comprises a polypeptide having at least 80, 90, 95, 99%, or 100% sequence identity to the amino acid sequence 230-426 of SEQ ID NO: 1, and the pore-forming unit comprises a polypeptide having at least 80, 90, 95, 99%, or 100% sequence identity to amino acid sequence 1-591 of SEQ ID NO: 2, and the payload unit comprises a polypeptide having at least 80, 90, 95, 99%, or 100% sequence identity to amino acid sequence of SEQ ID NO: 3.

In another embodiment, in a composition for delivering an agent to a target cell comprising a target cell binding unit, a pore-forming unit and a payload unit, the target cell binding unit and the pore-forming unit are covalently linked to form a polypeptide having at least 80, 90, 95, 99%, or 100% sequence identity to the amino acid sequence of SEQ ID NO: 4, and the payload unit comprises a polypeptide having at least 80, 90, 95, 99%, or 100% sequence identity to the amino acid sequence of SEQ ID NO: 3.

In another embodiment, the disclosed composition may be administered to a subject by injection, wherein the subject contains the target cell(s).

In another embodiment, a polynucleotide encoding a polypeptide is disclosed, wherein the polypeptide has at least 80, 90, 95, 99%, or 100% identity to a polypeptide selected from the group consisting of SEQ ID NOs 1-6. In one aspect, the polynucleotide may be carried on a vector. In one aspect, the vector may be capable of replicating itself.

In another embodiment, a host cell comprising the polynucleotide is also disclosed. The host cell may be used to produce the composition for delivering the agent to a target cell. In another embodiment, the host cell may be introduced into a subject for delivery of the agent. In another embodiment, for purpose of this disclosure, the host cell may be a bacterium, or a virus.

BRIEF DESCRIPTION OF THE FIGURES

FIG. 1 shows (a) Molecular steps of intoxication by the native C2 toxin; and (b) Model of neural delivery based upon the C2II-C1 and C2It transport system.

DETAILED DESCRIPTION

Figure 2:
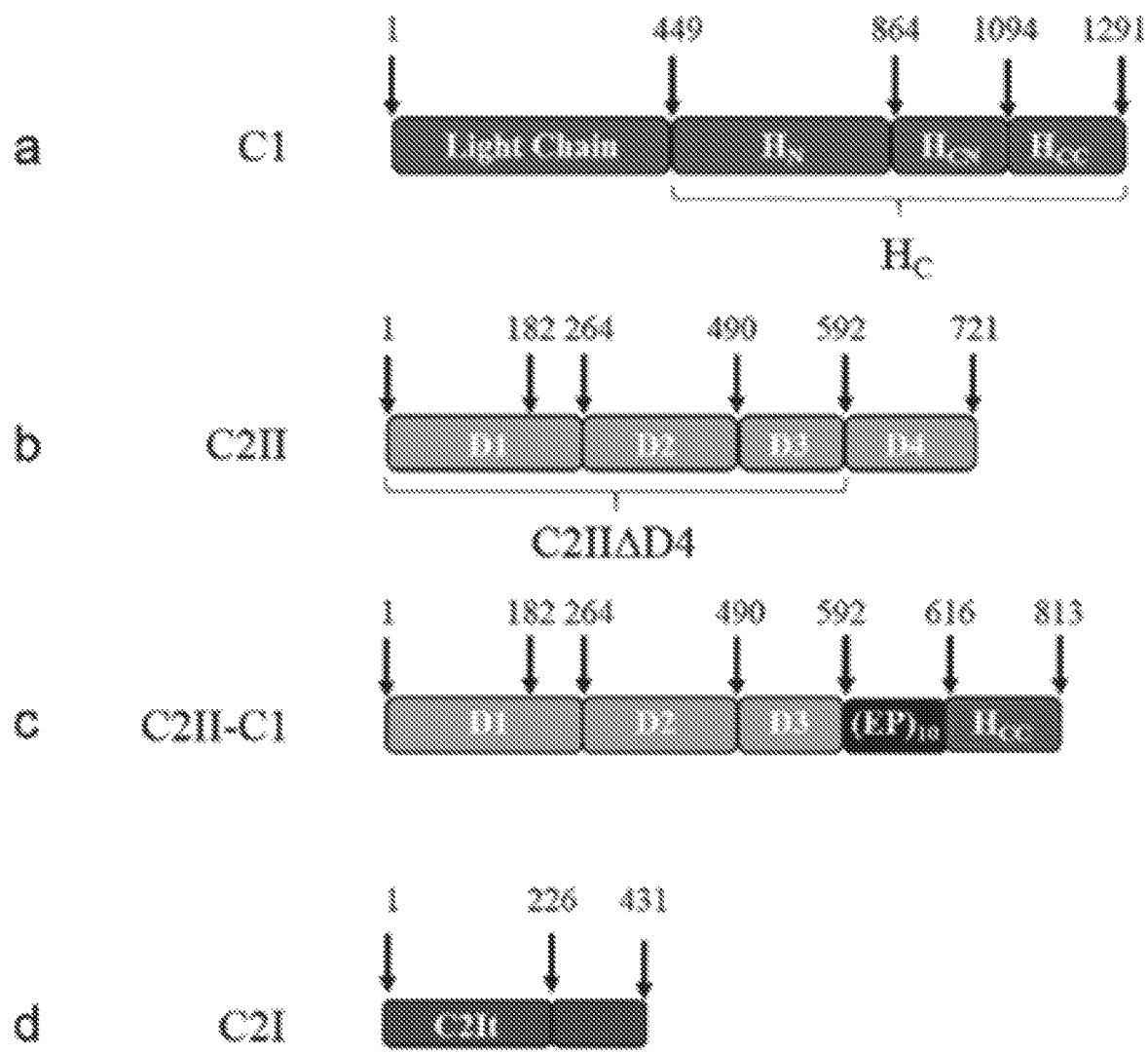
FIG. 2 shows protein domains of *C. botulinum* C1, *C. botulinum* C2II, fusion C2II-C1, and C2I. Numbers correspond to amino acid residues of each protein. (a) BoNT C1 has a linked enzymatic payload domain (light chain) and a binding/translocation domain (heavy chain). (b) The C2II binding/translocation component has four domains. Amino acid residue 182 indicates the trypsin cleavage position for activation of C2II into C2IIa. Domain 4 (D4) was removed to produce C2IIΔD4 as the translocation domain for C2II-C1. (c) The fusion C2II-C1 (SEQ ID NO: 4) was made by linking C2IIΔD4 (amino acids 1-591 of SEQ ID NO: 2) and BoNT C1 $H_{CC}$ (amino acids 230-426 of SEQ ID NO: 1) with an $(EP)_{10}$ linker flanked by glycine-serine residue pairs on both sides (SEQ ID NO: 5). Amino acid 182 is the activation site for C2II-C1. (d) The native C2I enzymatic payload of the C2 toxin and truncated C2It domain. Amino acids 299, 348, 387 and 389 are essential for ADP-ribosylation activity of C2I (SEQ ID NO: 3) and are therefore not present in C2It (SEQ ID NO: 6).

Compositions and methods for delivering molecular payloads to the cytosol of target cells are disclosed. Bacteria have evolved mechanisms to target cells and deliver toxic payloads to the cytosol of target cells. This mechanism may be modified and engineered to deliver beneficial payloads.

In general, there are two classes of AB-type bacterial toxins: linked and unlinked (binary). Linked toxins typically have a single chain protein containing both a toxin domain and a binding/translocation domain. Binary toxins typically have two separately expressed protein molecules, where the binding/translocation domain and the toxin domain assemble via non-covalent interactions.

For purpose of this disclosure, the term "derived" means a molecule is constructed based on another molecule and is identical, substantially identical or substantially similar in structure to that other molecule. In another aspect, the derived molecule typically performs identical, substantially identical or substantially similar functionality as the other molecule.

The term sequence identity is used to denote the similarity in amino acid or nucleotide sequence. Where a smaller molecule is compared to a larger molecule, the smaller molecule may be compared to the full-length or a partial fragment of the larger molecule.

Figure 1:
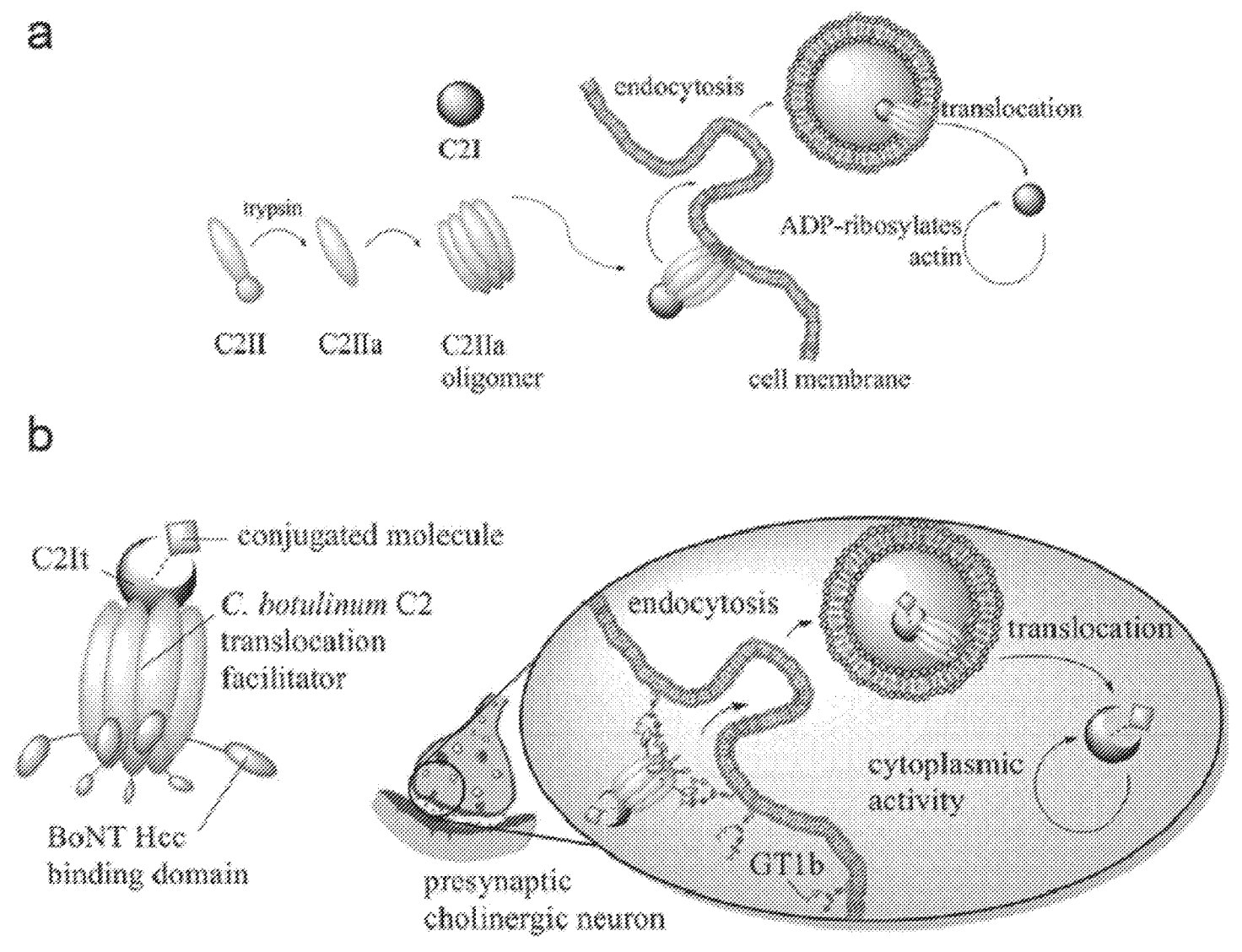

The native C2 toxin is composed of two separate proteins. The B domain protein (C2II) binds target cells and translocates the A domain (C2I, the payload). The A domain is an ADP-ribosyltransferase that causes cell rounding and apoptosis initiated by ADP-ribosylation of cytoplasmic actin (FIG. 1a). C2II monomers are proteolytically processed to remove a 20 kDa segment from the N-terminus, which activates the binding/translocation domain into C2IIa. C2IIa monomers then spontaneously oligomerize and bind the cell surface via interactions with asparagine-linked glycans on the cell membrane. The A domain, C2I, binds to the C2IIa oligomers and the C2IIa/C2I complex is internalized by clathrin and Rho-dependent mechanisms. Acidification of the early endosome causes membrane pore formation by C2IIa oligomers, through which C2I is transported into the cytoplasm.

For therapeutic development, engineering of a binary toxin has certain advantages because the binding/translocation domain and the payload domain may be separately expressed and purified. The C2 toxin from *C. botulinum* is a binary structure, but is nonspecific as it binds a variety of cells and necessitates N-linked glycans for intoxication (i.e., it is not a specific neurotoxin). Disclosed here are methods to engineer the C2 toxin binding domain by retargeting to neural cells. More specifically, the target binding domain from the C1 botulinum neurotoxin may be used. The binding domain from the C1 botulinum neurotoxin has been previously applied as a targeting component for drug delivery to peripheral neural tissue in linked toxin designs and as liposomal surface modifications.

In one embodiment, binding domain replacement of the C2 toxin requires that the retargeted binding/translocation component retain its ability to oligomerize upon activation, bind to the new targeting moiety on the cell surface, and translocate the payload into the cytosol of the target cell. The natural binding domain of the C2 toxin is located at the C-terminal end of the molecule and is designated as D4 (see FIG. 2b). In one aspect, D4 is not required for oligomerization because translocation pores can be formed in artificial membranes even when D4 is absent. In another aspect, D4 is deleted from C2II and replaced with the BoNT C1 binding domain that would target the molecule to peripheral neurons. The BoNT C1 Hcc (FIG. 2a) preferentially binds gangliosides GT1b and GD1b.

In another embodiment, BoNT/A N-terminal heavy chain domain (HCN) is not included in the chimeric C2II-C1. It has been shown that HCN may assist in the orientation of the toxin for association with the membrane by interacting with phosphatidylinositol phosphates. It is shown that that although HCN may be active in native BoNT translocation, it is not required in a chimeric C2II-C1 translocation event.

In another embodiment, the binding domain is taken from a linked toxin and inserted into the binding/translocation domain of a binary toxin. This configuration retarget the resulting molecule to neurons while maintaining the C2 toxin's mechanism of activation and translocation. It should be noted that a similarity exists between BoNT and C2 endocytosis and translocation mechanisms in that a clathrin/rho/dynamin-mediated endocytic-endosomal entry pathway characterized by pH-dependent protein conformational changes is implicated for both toxins.

In another embodiment, attempts have been made to express a soluble C2II-C1 fusion protein that would oligomerize when activated with trypsin. Direct fusion of the C1 $H_{CC}$ domain was not successful due to solubility problems. To remedy this limitation a flexible glycine-serine linker $(G_4S)_n$ was used but encountered similar issues. Finally, use of a rigid $(EP)_{10}$ linker resulted in a soluble fusion protein that is compatible with activation and oligomerization. SDS-PAGE confirmed that the C2II-C1 fusion protein could be activated by limited trypsin digestion and then oligomerize. Western blotting is used to confirm that the C1 $H_{CC}$ domain is incorporated into the oligomeric species. BoNT C1 antigenicity specific to the C2II-C1 oligomer and a decrease in electrophoretic mobility in comparison to C2IIΔD4 demonstrate that C1 $H_{CC}$ at the C-terminus of C2II-C1 does not prevent oligomerization and is compatible with limited trypsin digestion.

Figure 3:
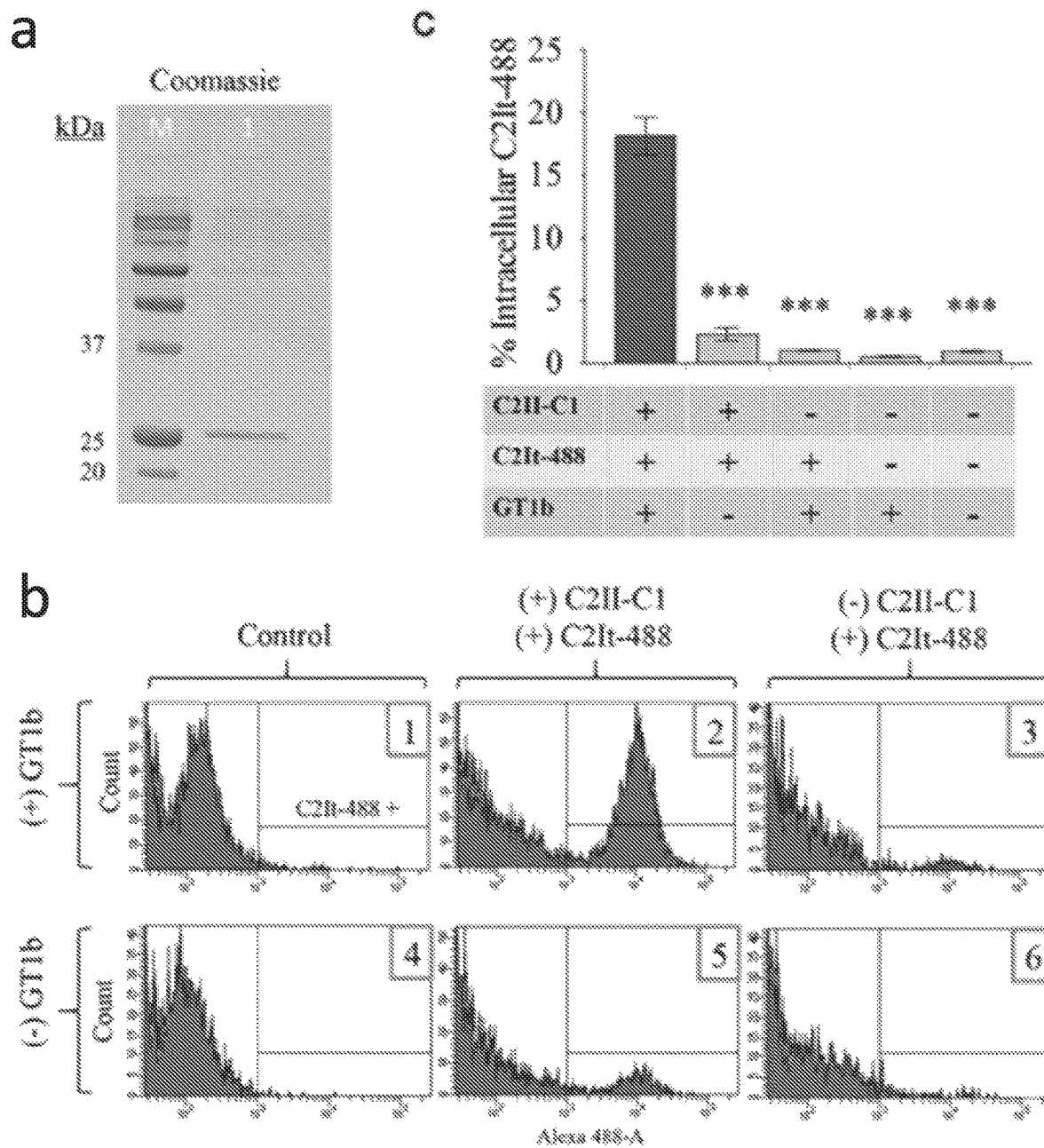
FIG. 3 shows Flow cytometry to evaluate C2II-C1-mediated uptake of C2It-488 to differentially GT1b-enriched cell populations. (a) Coomassie stained SDS-PAGE of purified C2It (~26 kDa). Lanes: M: molecular ruler, 1: soluble elution fraction after thrombin cleavage. (b) Indicated N2A cells were GT1b-enriched and subsequently incubated with recombinant proteins activated C2II-C1 (2 μg/mL) and C2It-488 (4 μg/mL) for 2 hours. Cells were then processed with pronase (1 μg/mL) to remove membrane-bound C2It-488. Samples were analyzed by a BD FACS Canto II flow cytometer using FACSDiva software. (c) Quantitative assessment of intracellular fluorescence by flow cytometry. Percentages are expressed as a mean±SEM (n=3) and statistical significance of GT1b-dependent uptake of C2It-488 mediated by C2II-C1 was calculated using Student's t-test by comparison to each control mean value. $p<0.005$.
Figure 4:
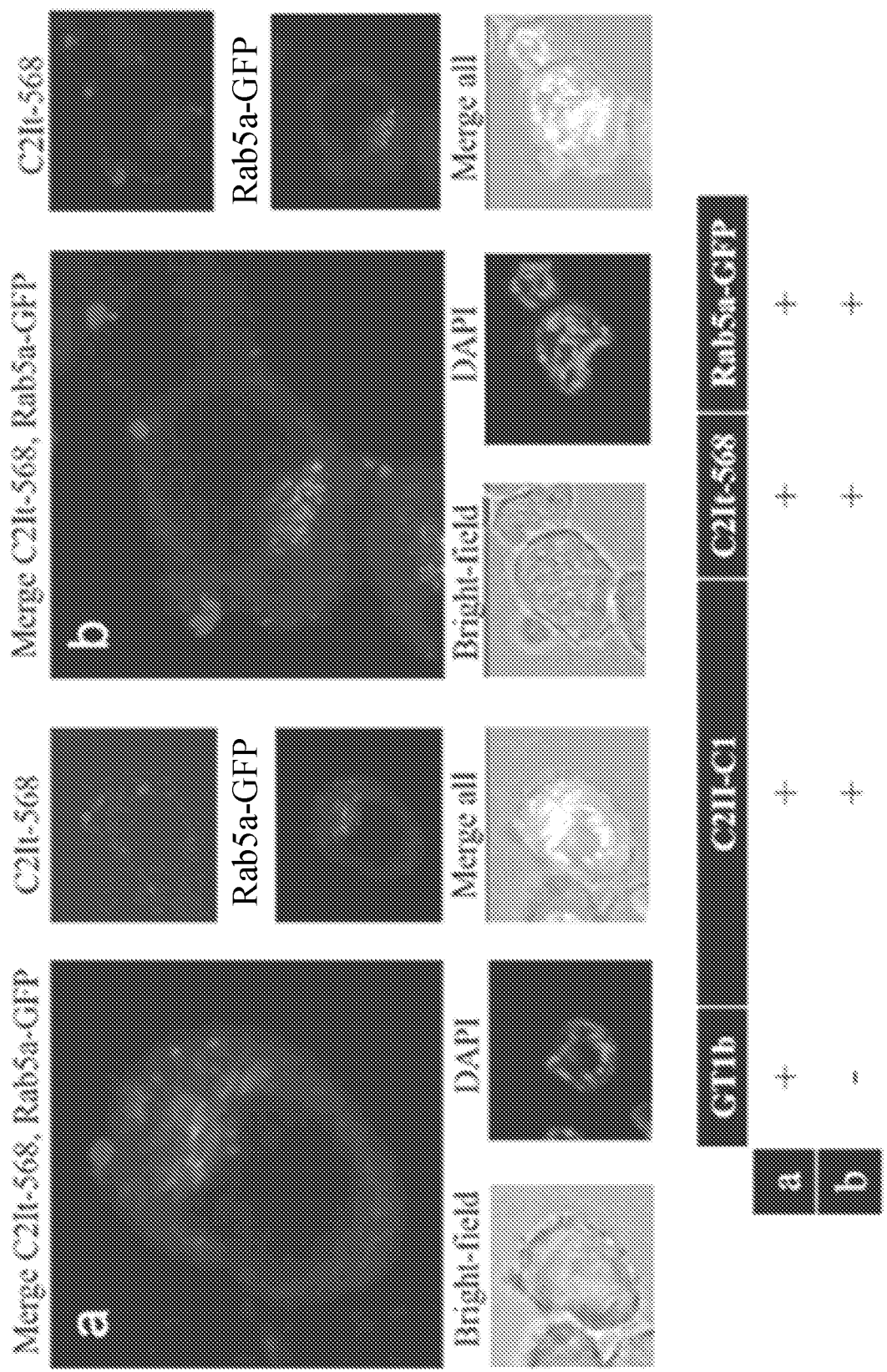
FIGS. 4 (*a*) and (*b*) show CLSM images of GT1b differentially GT1b-enriched N2A cells treated with C2II-C1 and C2I-568. All images were captured with 60× oil lens with 2× optical zoom. N2A populations were treated with a Rab5a-GFP early endosome marker (green) for 24 hr and stained with DAPI. Activated C2II-C1 (2 μg/mL) C2It-568 (red, 4 μg/mL) and GT1b (50 μg/mL) were incubated for 2 hours. (a) Cells were enriched with GT1b for 4 hr prior to addition of proteins. (b) Cells were not GT1b-enriched prior to addition of proteins.

To quantify and visualize binding and internalization of a payload by C2II-C1, a fluorescently labeled C-terminally truncated C2I-based payload, C2It (FIG. 2d), was constructed for use in flow cytometry and microscopy experiments. C2It that was composed of amino acids 1-226 of C2I (not containing the ADP-ribosylating active site residues), was fluorescently labeled in two separate versions with Alexa Fluor 488 (C2It-488) and 568 (C2It-568) by amine reactive chemistry. Previously, BoNT C1 $H_C$ entry was shown to be GT1b-dependent in N2A cells that were artificially enriched for GT1b[30], and this strategy was adapted to study targeting by the C2II-C1 fusion protein. If the engineered B component, C2II-C1, were activated, oligomerized and associated with the fluorescently labeled A component, C2It, GT1b-dependent uptake of fluorescently labeled C2It should be observed. This cellular model does not employ electrostimulation as previously described to enhance BoNT C1 intoxication because entry alone was presumed to be sufficient for the non-neural-specific C2 component of the fusion to promote translocation activity. For flow cytometry, a culture of N2A cells was enriched with GT1b while another was not, both cultures were incubated with activated C2II-C1 and C2It-488, and then both cultures were treated with pronase to remove extracellular proteins prior being analyzed. Cells with intracellular fluorescence above $10^3$ absorbance units were counted by flow cytometry and repeated results showed that N2A cell populations enriched with the binding domain receptor GT1b preferentially took up C2II-C1-delivered fluorescent C2It (FIG. 3). The results shown here indicate that the BoNT C1 $H_{CC}$ can be used to replace another toxin binding domain and result in a GT1b-dependent entry specificity. To confirm this uptake is dependent on GT1b and to determine subcellular localization within N2A cells, confocal microscopy is employed (FIG. 4). C2It-568 preferentially enters GT1b-enriched cells and does not colocalize with fluorescently labeled early endosomes. Escape from the early endosome by transport of C2It through the pore created by the translocation domain is a determinant of payload delivery to the cytosol. These results are consistent with the expected association between the engineered payload and binding/translocation domain by GT1b-specific delivery of C2It by C2II-C1. Lack of colocalization of early endosomes with C2It-568 (FIG. 4(a)) provides evidence to pursue other payloads with the intent of cytosolic delivery to manipulate the cytosome.

To deliver an active enzyme to the cytosol by the C2II-C1 fusion, the native C2 toxin A component, C2I may be produced. The C2I enzyme is known to cause cell rounding in eukaryotic cells by ADP-ribosylation of cytosolic actin. The effect of C2I is tested after delivery by C2II-C1 to human glioblastoma A172 and HeLa cell lines that are enriched with the ganglioside GT1b. A greater than two-fold increase in cell rounding of GT1b-enriched cell populations is found for both cell lines when compared to controls lacking GT1b enrichment. By comparison, payload-induced cell rounding of synchronized HeLa cells in the presence of the fusion translocator C2II-C1 is less efficient than reported by Barth et al. in the presence of the native C2II translocation domain. A truncated form of C2II-C1 characterized during expression may have incorporated into C2II-C1 oligomers, which may result in a decrease in binding efficiency. Although an apparent lack of monomeric C2II-C1 in final purification fractions is evident by SDS-PAGE, it is possible that monomeric C2II-C1 dissociated or not incorporated into oligomers compete for binding with the functional form of the oligomeric delivery system. These findings confirm the native cytosolic activity of the C2I enzyme specifically delivered by C2II-C1 in a GT1b-dependent manner.

In another embodiment, alternate payloads based on modified C2It may be used in delivery applications of the C2II-C1 fusion protein affecting the natural targets of BoNTs (FIG. 1b). A minimal region of amino acid residues 1-87 in the C2I component is required for complementary activity with the native C2II translocation domain. Translocation of non-canonical polypeptides may also be possible with modified C2I, similar to payload development work recently conducted with anthrax lethal factor. This disclosure provides the basis of exploring other binding specificities and payload domains for additional applications.

The following examples are provided to illustrate the present disclosure, but are not intended to be limiting. The chemicals and physical parameters are presented as typical reagents or parameters, and various substitutions or modifications may be made in view of this disclosure by one of skills in the art without departing from the principle and spirit of the present invention.

EXAMPLES

Example 1 Construction and Expression of Chimeric Constructs: C2II-C1, C1 HCC, C2ΔD4, C2It and C2I Plasmid pUC57-C2II-C1 HCC was purchased as a codon-optimized gene synthesis product. It consists of the C2II gene truncated by seven C-terminal amino acids upstream to the C1 HCC sequence, representing BoNT C1 amino acids Y1094-E1291. Primers C2IIΔD4F and C2IIΔD4-GS(EP)R amplified the gene corresponding to C2II amino acids M1-T592 and added a 5' BamHI extension and 3' glycine-serine-(EP) linking region to be used for overlapping PCR with the C1 $H_{CC}$ domain. The BoNT C1 $H_{CC}$ gene was PCR amplified with primers (EP)GS-C1 $H_{CC}$F and C1 $H_{CC}$R to contain a 3' EcoRI restriction site. A second round of PCR was performed using GS(EP)$_{10}$GSF and C1 $H_{CC}$R to extend the 5' amplicon of the C1 $H_{CC}$ to complement the 3' of the C2IIΔD4-GS(EP) sequence. The two resulting fragments were fused by overlapping PCR to yield C2IIΔD4-GS(EP)$_{10}$GS-C1 $H_{CC}$ (C2II-C1). To generate C1 $H_{CC}$, PCR amplification was performed on the pUC57-C2II-C1 $H_{CC}$ template using primers C1 $H_{CC}$F and C1 $H_{CC}$R. To generate C2IIΔD4, primers C2ΔD4F and C2ΔD4R were used to amplify the C2II gene without domain 4. Plasmid pUC57-C2It, was purchased as a codon optimized gene synthesis product. C2It (corresponding to C2I amino acids 1-226, PDB 2J3V) was directly subcloned into pGex-2T using BamHI and EcoRI restriction sites. Full length C2I (corresponding to C2I amino acids 1-431) was generated by overlapping PCR by fusion of C2It to DNA amplified from a synthetic DNA using C2IF and C2IR as flanking primers and C2IOF and C2IOR as overlapping primers. All final PCR products were digested by BamHI and EcoRI and ligated into pGex-2T. DH5α was transformed by electroporation to propagate C2II-C1, C1 $H_{CC}$, C2IIΔD4, C2It and C2I as N-terminal GST fusions. DNA construct identities were confirmed with sequencing. Primer sequences are listed in Table 1.

TABLE 1

| Primer sequences | |
|---|---|
| C2IIΔD4F | CGCGGATCCATGCTGGTCTCC (SEQ ID NO: 7) |
| C2IIΔD4-GS(EP)R | CCGGCTCTGGTTCCGGTTCAGAACCGGTGATCACTTT GACCA GAATATTCATG (SEQ ID NO: 8) |
| (EP)GSC1 $H_{CC}$F | CCAGAACCAGAGCCAGAACCAGGTTCTACCAACGTTG TCAAA GACT ATTGGGG (SEQ ID NO: 9) |
| C1 $H_{CC}$R | CGGGAATTCTTATTCTGAAACCGGGAC (SEQ ID NO: 10) |
| GS(EP)$_{10}$GSF | AACCGGAACCAGAGCCGGAACCGGAACCGGAACCGG AGCCA GAACCAGAGCCAGAACC (SEQ ID NO: 11) |
| C1 $H_{CC}$F | CGCGGATCCATGGGCACCAACGTTGTCAAAGACTAT TGG (SEQ ID NO: 12) |
| C2IIΔD4R | CGGGAATTCTTA GGTGATCACTTTGACCAG (SEQ ID NO: 13) |
| C2IF | CGCGGATCCATGCCGATTATTAAAGAACCGATTGACT TCATC AACAAACCGG (SEQ ID NO: 14) |
| C2IR | CCGGAATTCTTAGATTTCTTTGTTTTGGATACCTTCAG CATCA AT (SEQ ID NO: 15) |

TABLE 1-continued

Primer sequences

| | |
|---|---|
| C2IOF | GCAAGAACTGGACTTTTACAACAAAGGCTCGGAAGCCT GGGG TGCGGAAAACTATG (SEQ ID NO: 16) |
| C2IOR | CATAGTTTTCCGCACCCCAGGCTTCCGAGCCTTTGTTG TAAAA GTCCAGTTCTTGC (SEQ ID NO: 17) |

Fusion proteins were overproduced in *E. coli* BL21 (DE3). All cell lines were grown in 400 mL LB, 100 µg/mL ampicillin at 37° C. until induction at $OD_{600}$~0.5 with 0.5 mM IPTG at 25° C. for 16 hr. Cells were harvested in 100 mL aliquots and the pellets were stored at −20° C. Cells were resuspended in PBS, 1% Triton, pH 7.4, and a French press was used to lyse aliquoted cells by three passes at 10,000 psi. Cell debris was removed by ultracentrifugation at 80,000×g for 20 minutes at 4° C. Immobilized glutathione agarose (Genscript) was used to affinity purify GST fusion protein supernatants in batches using 150 µL of washed resin per 15 mL of culture supernatant and an incubation time of 1 hr at 4° C. Resin was washed with PBS pH 7.4 to remove unbound protein. Proteins were cleaved from the GST tag according to manufacturer's recommendations by bovine thrombin and separated from the purification resin by filtration using glass wool in a syringe. C2II-C1 was further processed by incubation with trypsin for 30 mins at a 1:5 enzyme to substrate ratio concluding with trypsin deactivation by trypsin inhibitor as described to activate recombinant C2II.

C2II-C1, C2IIΔD4, C1 $H_{CC}$, C2I and C2It were separated by SDS-PAGE using a 10% polyacrylamide gel or by a 4-12% gradient Bis-Tris Gel. An anti-BoNT C1 polyclonal antibody (Metabiologics Inc., Madison, Wis.) was used to identify C2II-C1 using purified C1 $H_{CC}$ as a positive control and C2IIΔD4 as a negative control. Proteins were separated by SDS-PAGE, transferred to a nitrocellulose membrane in Towbin buffer, blocked with 5% powdered milk in PBS-tween buffer and then probed with a 1:5,000 dilution of a 1 µg/ul anti-BoNT C1 antibody in 0.5% powdered milk in PBS-tween. Anti-rabbit HRP secondary antibody in 0.5% powdered milk, PBS-tween (1:5,000), was used for signal detection with ECL blotting substrate.

Neuro-2a cells (N2A) (ATCC, CCL-131) were cultured in Eagle's minimal essential medium (EMEM) supplemented with 10% (v/v) fetal bovine serum (FBS) and penicillin-streptomycin. A172 cells were grown in DMEM supplemented with 10% (v/v) FBS and penicillin-streptomycin (100 U/mL-100 µg/mL). HeLa cells (ATCC, CCL-2) were cultured in EMEM supplemented with 10% FBS and penicillin-streptomycin. HeLa cells were synchronized by double thymidine block with deoxycytidine release prior to ganglioside enrichment. Ganglioside-enriched cells were prepared by sonicating 50 µg/mL GT1b (Enzo Life Sciences, Farmingdale, N.Y.) in low-serum (0.5% FBS) culture medium for 20 min at room temperature. Cells were subsequently incubated 4 hr with GT1b. Prior to addition of recombinant proteins, cells were washed three times with PBS to remove free ganglioside from the culture medium. Flow cytometry with a 488 nm laser line and 586/42 bandpass filter on a BD FACSCanto II was used to confirm HeLa synchronization by staining of DNA with propidium iodide. 10,000 cells/events were counted and statistical significance of average fluorescence per cell was determined by Student's t-test (n=3).

Amine reactive Alexa Fluor dyes were dissolved in anhydrous DMSO (10 mg/mL) and stored as aliquots at −20° C. Purified proteins were concentrated to >5 mg/mL and adjusted to pH 8.5-9.0 with addition of 1 M sodium bicarbonate. Alexa Fluor in anhydrous DMSO was added to protein solutions with continuous stirring for 1 hr at room temperature. Excess Alexa Fluor and DMSO was removed by gel filtration (G-25 resin). Labeled proteins were ultracentrifuged at 80,000×g and subsequently assessed for degree of labeling by spectrophotometry before and after ultracentrifugation. A degree of labeling greater than 1 fluorescent molecule per molecule of protein was used as a quality control cutoff and there was no visible pellet or appreciable change in spectrophotometric qualities after ultracentrifugation.

N2A cells were grown in 24 well culture plates to ~80% confluence. Cells were enriched with GT1b as indicated in FIG. 3c. Activated C2II-C1 was added at 4 µg/mL and C2It-488 at 2 µg/mL using a 0.5 mL working volume and incubated with cells for 2 hours. Cells were washed twice with PBS, then trypsinized and harvested. Cells were centrifuged and resuspended in PBS with pronase (1 µg/mL) and incubated on ice for 5 minutes. Protease inhibitor cocktail was then added and cells were centrifuged and resuspended in PBS with inhibitor cocktail. 10,000 events/cells were then counted by BD FACS Canto II flow cytometer using a 488 laser line and 530/30 emission band-pass filter. C2It-488 positive cells (greater than the absorbance threshold $10^3$ absorbance units) were counted and evaluated as a percentage of total cells. Replicated experiments were evaluated by Student's t-test (n=3).

Collagen-coated 12 mm no. 1 coverslips were placed into 24-well culture plates and seeded with N2A cells. N2A cells were grown to ~80% confluence. Purified C2It was labeled with Alexa Fluor 568 succinimidyl ester (C2It-568) instead of Alexa Fluor 488 to allow for discrimination from the early endosome marker. The baculovirus transduction system, BacMam 2.0 Cell Lights Rab5a-GFP early endosomal marker (Life Technologies), was added ~24 hr prior to GT1b enrichment. Cells were then enriched with GT1b as described in our methods. Recombinant proteins were added after washing of cells to remove free gangliosides. Activated C2II-C1 was added at 4 µg/mL and C2It-568 at 2 µg/mL using a 0.5 mL working volume and incubated with cells for 2 hours. Cells were washed with PBS, fixed with 4% paraformaldehyde and stained with DAPI. After processing, an Olympus Inverted IX-81 Microscope was used with an Olympus FV 500 confocal laser scanning microscope in sequence mode with laser lines 405 nm (blue), 488 nm (green) and 543 nm (red) to capture fluorescence images. Corresponding emission barriers used were 430-460 nm, 505-550 nm and 560-610 nm respectively. Transmitted light was used for cell morphology, and all images were captured using a 60× oil lens with 2× optical zoom. Contrast of all images was increased by 20%. Human glioblastoma A172 cells (ATCC, CRL-1620) were grown in 24 well culture plates to ~60% confluence to reduce cell rounding observed at higher confluence. HeLa cells were synchronized as described in the previous section. Both cell lines were enriched with GT1b as described in our methods at 50 µg/mL. C2II-C1 was added at 40 µg/mL and C2I was added at 20 µg/mL using a 0.5 mL working volume and incubated with cells for 7 hours. Pictures of cells were taken using an Amscope IN300TC inverted stereo microscope at 40× using Amscope MT v 3.0.0.5 soft-ware. Rounded cells were counted and determined as a percentage of total cells in the frame. The experiment was replicated three times and evaluated for statistical significance with Student's t-test (n=3). Institutional biosafety committee approval was obtained prior to execution of experiments with C2I in a biosafety level 2 laboratory due to anticipated toxicity when combined with C2II-C1.

Example 2 Retargeting the *Clostridium botulinum* C2 Toxin to Neuronal Cytosol

Multiple recombinant protein constructs were expressed and purified using *E. coli* that were based on the BoNT sub-serotype C1 neurotoxin and the ADP-ribosylating C2 toxin. The native BoNT C1 is depicted in FIG. 2a, and the native C2II binding/translocation domain is depicted in FIG. 2b. C2 toxin with C-terminal deletion of domain 4 (C2IIΔD4) and the C1 neurotoxin binding domain C1 $H_{CC}$ were produced for use as controls. The C2IIΔD4 and C1 $H_{CC}$ of BoNT C1 (1094-1291) were linked with a glutamate-proline ten-repeat peptide linker $(EP)_{10}$ to generate C2II-C1 (FIG. 2c). In addition, two C2I-based payloads were constructed including a non-toxic C2It (1-226) that excludes the active enzyme site and a full length C2I (1-431) (FIG. 2d).

Cleavage of the glutathione affinity tag (GST) and activation of C2II-C1 by trypsin into oligomers was confirmed. *E. coli* BL21(DE3) cells were lysed and ultracentrifuged to remove insoluble proteins and the supernatant was passed over the affinity resin. The resin was then washed extensively, and protein-bound resin was loaded to examine the mass of the full length resin-bound protein and the extent of thrombin cleavage. The resin was then treated with thrombin to cleave the GST tag. Proteins were then eluted from the resin and treated with trypsin. The trypsin-activated C2II-C1 monomers oligomerized as indicated by a shift in electrophoretic migration from an observed mass of ~90 kDa to a much greater mass than 250 kDa. Activated C2IIΔD4 was also produced with the same method and compared to activated C2II-C1. The heptameric form of C2II-C1 had an expected molecular mass of ~497 kDa, and heptameric C2ΔD4 had as an expected molecular mass of ~350 kDa. The C2II-C1 oligomer had a higher mass than that of C2IIΔD4 oligomer, as expected. The oligomerized forms of C2II-C1 and C2ΔD4 maintained stability in SDS during electrophoresis and dissociated partially with the addition of heating. An additional band was identified during purification with anti-BoNT C1 antigenicity. However, after extensive heating of C2II-C1 oligomers, it was determined the dissociated composition was predominantly of full-length C2II-C1 monomers.

Western blotting was conducted of oligomerized C2II-C1 and C2IIΔD4 Proteins were then probed with an anti-BoNT C1 antibody. BoNT C1 HCC (MW ~23 kDa) was used as a positive control. C2II-C1 oligomers cross-reacted with the anti-BoNT C1 antibody, while the oligomerized C2IIΔD4 did not cross-react. This confirmed that BoNT C1 HCC was successfully fused to C2IIΔD4 via the (EP)10 repeat linker in the oligomeric state.

Neural Targeting of Fluorescently Labeled C2It Payloads by C2II-C1.

The binding and payload internalization that were mediated by the C2II-C1 binding/translocation component was investigated using a fluorescently labeled C2I-based payload, C2It (FIG. 2d), to populations of cells with and without the GT1b ganglioside receptor. Murine neuroblastoma Neuro-2A (N2A) cells do not naturally present GT1b on the cell surface, but can be artificially enriched. After payload C2It was purified (FIG. 3a), an Alexa Fluor 488 succinimidyl ester label was conjugated to the protein (C2It-488). C2It and activated C2II-C1 were incubated with differentially GT1b-enriched N2A cells. After removal of extracellular proteins by enzymatic digestion, flow cytometry was used to quantitate internalized C2It-488. The highest number of cells with increased fluorescence corresponded to GT1b enrichment and addition of C2II-C1 (FIG. 3b panel 2). Background uptake of C2It without C2II-C1 in the presence and absence of GT1b was minimal. Enrichment alone with GT1b did not give significantly increased background fluorescence (FIG. 3b panels 1, 4). Uptake of the C2It-488 payload alone was also minimal (FIG. 3b panels 3, 6). The highest non-target uptake (~2%) occurred in the population with C2II-C1 and C2It without GT1b (FIG. 3b panel 5). Student's t-test determined that the dependence of C2It-488 uptake on C2II-C1 and GT1b was significant with p-values <0.05 between experiments. Overall, an intracellular C2It-488 delivery efficiency of ~18% (percentage of cell population) was achieved in the presence of GT1b and C2II-C1 (FIG. 3c).

After quantitation of binding and internalization by flow cytometry, C2It delivered by activated C2II-C1 to targeted cells was visualized by confocal fluorescence light microscopy to determine intracellular localization. C2It was conjugated to an Alexa Fluor 568 fluorescent dye (C2It-568). Channel separated imaging was conducted of C2It-568 (red), Rab5a-GFP early endosomal marker (green), and DAPI nuclei (blue). It was observed that an intracellular C2II-C1-delivered C2It-568 colocalized at a low level with early endosomes when cells were enriched with GT1b (FIG. 4(a)). This result was consistent with endosomal escape of C2It by an active translocation domain. Without GT1b, C2It-568 signals were confined generally to the outside of the cell with low levels of reporter associated with early endosomes (FIG. 4(b)). These findings are consistent with the binding/internalization flow cytometry data (FIG. 3b,c). Additional control permutations lacking C2II-C1, GT1b or C2It-568 did not achieve intracellular delivery of C2It reporters with early endosomal dissociation.

Retargeting of the Native C2I Enzyme by C2II-C1.

Figure 5:
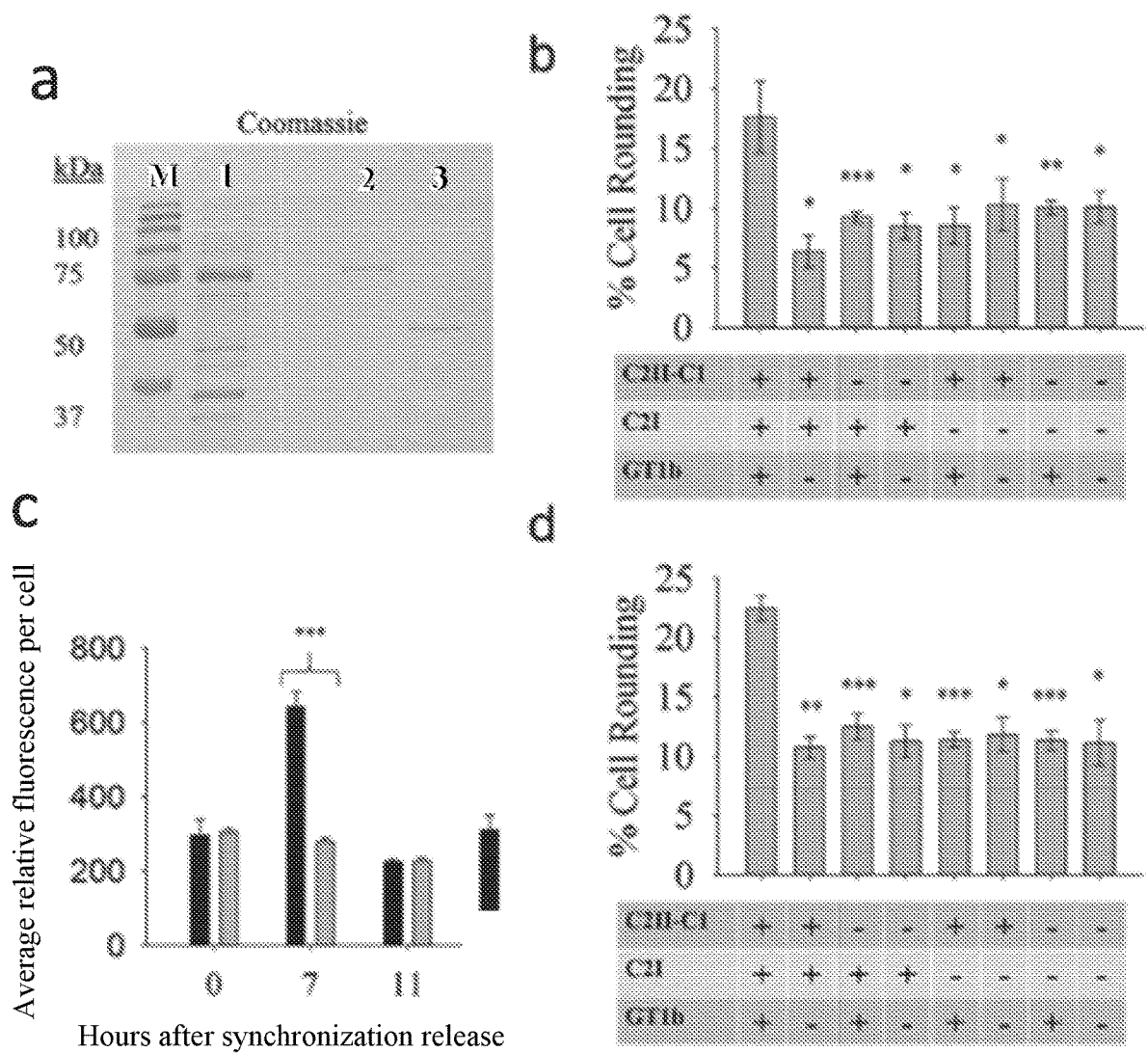
FIG. 5 shows Cell rounding of differentially GT1b enriched cell populations by C2I mediated by C2II-C1. (a) Coomassie stained SDS-PAGE of purified C2I. Expected masses: C2I-GST (~75 kDa), C2I (49 kDa) molecular ruler, 1: lysis supernatant, 2: purification resin prior to thrombin cleavage, 3: soluble elution fraction after thrombin cleavage. (b) A172 glioblastoma cells were grown to ~60% confluence and enriched as indicated with or without GT1b. (c) Flow cytometry of synchronized HeLa cells stained with propidium iodide with and without release from thymidine block over time was used to confirm progression of S phase DNA synthesis after removal of excess thymidine and addition of deoxycytidine for release. (d) Cell rounding of differentially GT1b-enriched synchronized HeLa cells.

Delivery of an active enzyme to the cytosol was determined by cell rounding caused by native C2I payload in both human glioblastoma A172 and synchronized HeLa cell lines differentially enriched with GT1b. Full length C2I was purified (FIG. 5a), combined with activated C2II-C1, and then added to cell line cultures for seven hours. Cell rounding was determined to be 2.8-fold higher than the non-GT1b enriched A172 cell population (FIG. 5b). Delivery-dependent cell rounding of synchronized HeLa cells was investigated as a non-neural cell line enriched with GT1b for a comparison to previous data of the wild type C2II without GT1b enrichment previously reported by Barth et al. *Infect. Immun.* 67, 5083-5090 (1999). Flow cytometry methods confirmed the synchronization of HeLa cells in the early S-phase by quantitation of DNA (FIG. 5c). In synchronized HeLa cells, rounding was 2.1-fold above the non-GT1b enriched population. (FIG. 5d). Student's t-test was used to evaluate the experimental significance between experiments. Comparing control populations to the GT1b-enriched population produced p-values <0.05.

List of Sequences of SEQ ID NOs 1-6:

```
List of sequences of SEQ ID NOs 1-6:

SEQ ID NO: 1 -
NNINDSKILSLQNRKNTLVDTSGYNAEVSEEGDVQLNPIFPFDFKLGSSG

EDRGKVIVTQNENIVYNSMYESFSISFWIRINKWVSNLPGYTIIDSVKNN

SGWSIGIISNFLVFTLKQNEDSEQSINFSYDISNNAPGYNKWFFVTVTNN

MMGNMKIYINGKLIDTIKVKELTGINFSKTITFEINKIPDTGLITSDSDN

INMWIRDFYIFAKELDGKDINILFNSLQYTNVVKDYWGNDLRYNKEYYMV

NIDYLNRYMYANSRQIVFNTRRNNNDFNEGYKIIIKRIRGNTNDTRVRGG

DILYFDMTINNKAYNLFMKNETMYADNHSTEDIYAIGLREQTKDINDNII

FQIQPMNNTYYYASQIFKSNFNGENISGICSIGTYRFRLGGDWYRHNYLV

PTVKQGNYASLLESTSTHWGFVPVSE

SEQ ID NO: 2 -
MLVSKFENSVKNSNKNYFTINGLMGYYFENDFFNLNIISPTLDGNLTFSK

EDINSILGNKIIKSARWIGLIKPSITGEYILSTNSPNCRVELNGEIFNLS

LNTSNTVNLIQGNVYDIRIEQLMSENQLLKNYEGIKLYWETSDIIKEIIP

SEVLLKPNYSNTNEKSKFIPNNTLFSNAKLKANANRDTDRDGIPDEWEIN

GYTVMNQKAVAWDDKFAANGYKKYVSNPFKPCTANDPYTDFEKVSGQIDP

SVSMVARDPMISAYPIVGVQMERLVVSKSETITGDSTKSMSKSTSHSSTN

INTVGAEVSGSLQLAGGIFPVFSMSASANYSHTWQNTSTVDDTTGESFSQ

GLSINTAESAYINPNIRYYNTGTAPVYNVTPTTTIVIDKQSVATIKGQES

LIGDYLNPGGTYPIIGEPPMALNTMDQFSSRLIPINYNQLKSIDNGGTVM

LSTSQFTGNFAKYNSNGNLVTDGNNWGPYLGTIKSTTASLTLSLPDQTTQ

VAVVAPNFSDPEDKTPRLTLEQALVKAFRLEKKNGKFYFHGMEISANQKI

QVFLDRNTNVDFENQLKNTANKDIMNCIIKRNMNILVKVITFKENISSIN

IINDTNFGVESMTGLSKRIKGNDGIYRASTKSFSFKSKEIKYPEGFYRMR

FVIQSYEPFTCNFKLFNNLIYSNSFDIGYYDEFFYFYCNGSKSFFDISCD

IINSINRLSGVFLI

SEQ ID NO: 3 -
MPIIKEPIDFINKPESEAKEWGKEEEKRWFTKLNNLEEVAVNQLKNKEYK

TKIDNFSTDILFSSLTAIEIMKEDENQNLFDVERIREALLKNTLDRDAIG

YVNFTPKELGINFSIRDVELDRDISDETLDKVRQQIINQEYTKFSFISLG

LNDNSINESVPVIVKTRVPTTFDYGVLNDKETVSLLLNQGFSIIPESAII

TTIKGKDYILIEGSLSQELDFYNKGSEAWGAENYGDYISKLSHEQLGALE

GYLHSDYKAINSYLRNNRVPNNDELNKKIELISSALSVKPIPQTLIAYRR

VDGIPFDLPSDFSFDKKENGEIIADKQKLNEFIDKWTGKEIENLSFSSTS

LKSTPSSFSKSRFIFRLRLSEGAIGAFIYGFSGFQDEQEILLNKNSTFKI

FRITPITSIINRVTKMTQVVIDAEGIQNKEI

SEQ ID NO: 4 -
MLVSKFENSVKNSNKNYFTINGLMGYYFENDFFNLNIISPTLDGNLTFSK

EDINSILGNKIIKSARWIGLIKPSITGEYILSTNSPNCRVELNGEIFNLS

LNTSNTVNLIQGNVYDIRIEQLMSENQLLKNYEGIKLYWETSDIIKEIIP

SEVLLKPNYSNTNEKSKFIPNNTLFSNAKLKANANRDTDRDGIPDEWEIN

GYTVMNQKAVAWDDKFAANGYKKYVSNPFKPCTANDPYTDFEKVSGQIDP

SVSMVARDPMISAYPIVGVQMERLVVSKSETITGDSTKSMSKSTSHSSTN

INTVGAEVSGSLQLAGGIFPVFSMSASANYSHTWQNTSTVDDTTGESFSQ

GLSINTAESAYINPNIRYYNTGTAPVYNVTPTTTIVIDKQSVATIKGQES

LIGDYLNPGGTYPIIGEPPMALNTMDQFSSRLIPINYNQLKSIDNGGTVM

LSTSQFTGNFAKYNSNGNLVTDGNNWGPYLGTIKSTTASLTLSLPDQTTQ

VAVVAPNFSDPEDKTPRLTLEQALVKAFRLEKKNGKFYFHGMEISANQKI

QVFLDRNTNVDFENQLKNTANKDIMNCIIKRNMNILVKVITGSEPEPEPE

PEPEPEPEPEPEPGSTNVVKDYWGNDLRYNKEYYMVNIDYLNRYMYANSR

QIVFNTRRNNNDFNEGYKIIIKRIRGNTNDTRVRGGDILYFDMTINNKAY

NLFMKNETMYADNHSTEDIYAIGLREQTKDINDNIIFQIQPMNNTYYYAS

QIFKSNFNGENISGICSIGTYRFRLGGDWYRHNYLVPTVKQGNYASLLES

TSTHWGFVPVSE

SEQ ID NO: 5 -
GSEPEPEPEPEPEPEPEPEPEPGS

SEQ ID NO: 6 -
MPIIKEPIDFINKPESEAKEWGKEEEKRWFTKLNNLEEVAVNQLKNKEYK

TKIDNFSTDILFSSLTAIEIMKEDENQNLFDVERIREALLKNTLDRDAIG

YVNFTPKELGINFSIRDVELDRDISDETLDKVRQQIINQEYTKFSFISLG

LNDNSINESVPVIVKTRVPTTFDYGVLNDKETVSLLLNQGFSIIPESAII

TTIKGKDYILIEGSLSQELDFYNKG
```

While the disclosure has been particularly shown and described with reference to particular embodiments thereof, it will be understood by those skilled in the art that various other changes in the form and details may be made without departing from the spirit and scope of the disclosure. It is to be understood that various changes may be made in adapting the invention to different embodiments without departing from the inventive concepts disclosed herein and comprehended by the claims that follow.

REFERENCES

The contents of all cited references (including literature references, patents, patent applications, and websites) that may be cited throughout this application or listed below are hereby expressly incorporated by reference in their entirety for any purpose into the present disclosure. The disclosure may employ, unless otherwise indicated, conventional techniques of immunology, molecular biology and cell biology, which are well known in the art.

The present disclosure also incorporates by reference in their entirety techniques and methods well known in the field of molecular biology. These techniques include, but are not limited to, techniques described in the following publications:

1. Schiavo, G., Matteoli, M. & Montecucco, C. Neurotoxins affecting neuroexocytosis. Physiol. Rev. 80, 717-766 (2000).

2. Singh, B. R. et al. Clostridial neurotoxins as a drug delivery vehicle targeting nervous system. Biochimie 92, 1252-1259 (2010).
3. Vazquez-Cintron, E. J. et al. Atoxic derivative of botulinum neurotoxin A as a prototype molecular vehicle for targeted delivery to the neuronal cytoplasm. PLoS ONE 9, doi: e8551710.1371/journal.pone.0085517 (2014).
4. Zhang, P. et al. An efficient drug delivery vehicle for botulism countermeasure. BMC Pharmacol. 9, doi: 10.1186/1471-2210-9-12 (2009).
5. Ho, M. F. et al. Recombinant botulinum neurotoxin A heavy chain-based delivery vehicles for neuronal cell targeting. Protein Eng. Des. Sel. 24, 247-253 (2011).
6. Webb, R. P., Smith, T. J., Wright, P., Brown, J. & Smith, L. A. Production of catalytically inactive BoNT/A1 holoprotein and comparison with BoNT/A1 subunit vaccines against toxin subtypes A1, A2, and A3. Vaccine 27, 4490-4497 (2009).
7. Mechaly, A., McCluskey, A. J. & Collier, R. J. Changing the receptor specificity of anthrax toxin. mBio 3, e00088-00012, doi: 10.1128/mBio.00088-12 (2012).
8. Fahrer, J. et al. C2-streptavidin mediates the delivery of biotin-conjugated tumor suppressor protein P53 into tumor cells. Bioconjug. Chem. 24, 595-603 (2013).
9. Fahrer, J., Rieger, J., van Zandbergen, G. & Barth, H. The C2-streptavidin delivery system promotes the uptake of biotinylated molecules in macrophages and T-leukemia cells. Biol. Chem. 391, 1315-1325 (2010).
10. Fahrer, J. et al. Genetically engineered clostridial C2 toxin as a novel delivery system for living mammalian cells. Bioconjug. Chem. 21, 130-139 (2010).
11. Schleberger, C., Hochmann, H., Barth, H., Aktories, K. & Schulz, G. E. Structure and action of the binary C2 toxin from *Clostridium botulinum*. J. Mol. Biol. 364, 705-715 (2006).
12. Aktories, K. et al. Botulinum-C2 toxin ADP-ribosylates actin. Nature 322, 390-392 (1986).
13. Simpson, L. L. Molecular basis for the pharmacological actions of *Clostridium botulinum* type C2 toxin. J. Pharmacol. Exp. Ther. 230, 665-669 (1984).
14. Ohishi, I., Iwasaki, M. & Sakaguchi, G. Purification and characterization of 2 components of botulinum C2 toxin. Infect. Immun 30, 668-673 (1980).
15. Iwasaki, M., Ohishi, I. & Sakaguchi, G. Evidence that botulinum C2-toxin has 2 dissimilar components. Infect. Immun 29, 390-394 (1980).
16. Ohishi, I. Activation of botulinum C2 toxin by trypsin. Infect. Immun. 55, 1461-1465 (1987).
17. Nagahama, M. et al. Binding and Internalization of *Clostridium botulinum* C2 Toxin. Infect. Immun 77, 5139-5148 (2009).
18. Fritz, G., Schroeder, P. & Aktories, K. Isolation and characterization of a *Clostridium botulinum* C2 toxin-resistant cell line: evidence for possible involvement of the cellular C2II receptor in growth-regulation. Infect. Immun 63, 2334-2340 (1995).
19. Pust, S., Barth, H. & Sandvig, K. *Clostridium botulinum* C2 toxin is internalized by clathrin- and Rho-dependent mechanisms. Cell Microbiol. 12, 1809-1820 (2010).
20. Kaiser, E., Haug, G., Hliscs, M., Aktories, K. & Barth, H. Formation of a biologically active toxin complex of the binary *Clostridium botulinum* C2 toxin without cell membrane interaction. Biochemistry 45, 13361-13368 (2006).
21. Barth, H. et al. Cellular uptake of *Clostridium botulinum* C2 toxin requires oligomerization and acidification. J. Biol. Chem. 275, 18704-18711 (2000).
22. Haug, G. et al. Cellular uptake of *Clostridium botulinum* C2 toxin: Membrane translocation of a fusion toxin requires unfolding of its dihydrofolate reductase domain. Biochemistry 42, 15284-15291 (2003).
23. Chaddock, J. A. et al. Inhibition of vesicular secretion in both neuronal and nonneuronal cells by a retargeted endopeptidase derivative of *Clostridium botulinum* neurotoxin type A. Infect. Immun. 68, 2587-2593 (2000).
24. Blocker, D. et al. The C terminus of component C2II of *Clostridium botulinum* C2 toxin is essential for receptor binding. Infect. Immun. 68, 4566-4573 (2000).
25. Gill, D. M. Bacterial toxins-a table of lethal amounts. Microbiol. Rev. 46, 86-94 (1982).
26. Montecucco, C. & Schiavo, G. Mechanism of action of tetanus and botulinum neurotoxins. Mol. Microbiol. 13, 1-8 (1994).
27. Strotmeier, J. et al. The biological activity of botulinum neurotoxin type C is dependent upon novel types of ganglioside binding sites. Mol. Microbiol. 81, 143-156 (2011).
28. Simpson, L. L. The origin, structure, and pharmacological activity of botulinum toxin. Pharmacol. Rev. 33, 155-188 (1981).
29. Yowler, B. C. & Schengrund, C. L. Glycosphingolipids-Sweets for botulinum neurotoxin. Glycoconj. J. 21, 287-293 (2004).
30. Karalewitz, A. P. A., Fu, Z. J., Baldwin, M. R., Kim, J. J. P. & Barbieri, J. T. Botulinum neurotoxin serotype C associates with dual ganglioside receptors to facilitate cell entry. J. Biol. Chem. 287, 40806-40816 (2012).
31. Barth, H., Klingler, M., Aktories, K. & Kinzel, V. *Clostridium botulinum* C2 toxin delays entry into mitosis and activation of p34(cdc2) kinase and cdc25-C phosphatase in HeLa cells. Infect. Immun. 67, 5083-5090 (1999).
32. Varkouhi, A. K., Scholte, M., Storm, G. & Haisma, H. J. Endosomal escape pathways for delivery of biologicals. J. Control. Release 151, 220-228 (2011).
33. Sandvig, K. & van Deurs, B. Delivery into cells: lessons learned from plant and bacterial toxins. Gene Ther. 12, 865-872 (2005).
34. Verdurmen, W. P., Luginbuhl, M., Honegger, A. & Pluckthun, A. Efficient cell-specific uptake of binding proteins into the cytoplasm through engineered modular transport systems. J. Control. Release 200, 13-22 (2015).
35. Eckhardt, M., Barth, H., Blocker, D. & Aktories, K. Binding of *Clostridium botulinum* C2 toxin to asparagine-linked complex and hybrid carbohydrates. J. Biol. Chem. 275, 2328-2334 (2000).
36. Andreu, A., Fairweather, N. & Miller, A. D. *Clostridium* neurotoxin fragments as potential targeting moieties for liposomal gene delivery to the CNS. Chem Bio Chem 9, 219-231 (2008).
37. Edupuganti, O. P. et al. Targeted delivery into motor nerve terminals of inhibitors for SNARE-cleaving proteases via liposomes coupled to an atoxic botulinum neurotoxin. FEBS J. 279, 2555-2567 (2012).
38. Tsukamoto, K. et al. Binding of *Clostridium botulinum* type C and D neurotoxins to ganglioside and phospholipid-Novel insights into the receptor for clostridial neurotoxins. J. Biol. Chem. 280, 35164-35171 (2005).
39. Rummel, A. et al. Botulinum neurotoxins C, E and F bind gangliosides via a conserved binding site prior to stimulation-dependent uptake with botulinum neurotoxin F utilising the three isoforms of SV2 as second receptor. J. Neurochem. 110, 1942-1954 (2009).

40. Muraro, L., Tosatto, S., Motterlini, L., Rossetto, O. & Montecucco, C. The N-terminal half of the receptor domain of botulinum neurotoxin A binds to microdomains of the plasma membrane. Biochem. Biophys. Res. Commun. 380, 76-80 (2009).
41. Harper, C. B. et al. Dynamin inhibition blocks botulinum neurotoxin type A endocytosis in neurons and delays botulism. J. Biol. Chem. 286, 35966-35976 (2011).
42. Couesnon, A., Pereira, Y. & Popoff, M. R. Receptor-mediated transcytosis of botulinum neurotoxin A through intestinal cell monolayers. Cell Microbiol. 10, 375-387 (2008).
43. Simpson, L. L. Identification of the major steps in botulinum toxin action. Annu. Rev. Pharmacol. Toxicol. 44, 167-193 (2004).
44. Zhao, H. L. et al. Increasing the homogeneity, stability and activity of human serum albumin and interferon-alpha 2b fusion protein by linker engineering. Protein Expr. Purif 61, 73-77 (2008).
45. Bhandari, D. G., Levine, B. A., Trayer, I. P. & Yeadon, M. E. H-1-NMR study of mobility and conformational constraints within the proline-rich N-terminal of the LC1 alkali light chain of skeletal myosin. Correlation with similar segments in other protein systems. Eur. J. Biochem. 160, 349-356 (1986).
46. Evans, J. S., Levine, B. A., Trayer, I. P., Dorman, C. J. & Higgins, C. F. Sequenced-imposed structural constraints in the tonB protein of Escherichia coli. FEBS Lett. 208, 211-216 (1986).
47. Roditi, I. et al. Expression of Trypanosoma brucei procyclin as a fusion protein in Escherichia coli. Mol. Biochem. Parasitol. 34, 35-43 (1989).
48. Kroken, A. R. et al. Unique Ganglioside Binding by Botulinum Neurotoxins C and D-SA. FEBS J. 278, 4486-4496 (2011).
49. Heine, K., Pust, S., Enzenmüller, S. & Barth, H. ADP-Ribosylation of Actin by the Clostridium botulinum C2 Toxin in Mammalian Cells Results in Delayed Caspase-Dependent Apoptotic Cell Death. Infect. Immun 76, 4600-4608 (2008).
50. Barth, H., Roebling, R., Fritz, M. & Aktories, M. The binary Clostridium botulinum C2 toxin as a protein delivery system—Identification of the minimal protein region necessary for interaction of toxin components. J. Biol. Chem. 277, 5074-5081 (2002).
51. Rabideau, A. E., Liao, X., Akcay, G. & Pentelute, B. L. Translocation of Non-Canonical Polypeptides into Cells Using Protective Antigen. Sci. Rep. 5, 11944 (2015).
52. Laemmli, U. K. Cleavage of structural proteins during the assembly of the head of bacteriophage T4. Nature 227, 680-685 (1970).
53. Towbin, H., Staehelin, T. & Gordon, J. Electrophoretic transfer of proteins from polyacrylamide gels to nitrocellulose sheets: procedure and some applications. PNAS 76, 4350-4354 (1979).
54. Burnette, W. N. Western blotting-electrophoretic transfer of proteins from sodium dodecyl sulfate polyacrylamide gels to unmodified nitrocellulose and radiographic detection with antibody and radioiodinated protein-A. Anal. Biochem. 112, 195-203 (1981).
55. Ma, H. T. & Poon, R. Y. Synchronization of HeLa cells. Methods Mol. Biol. 761, 151-161 (2011).
56. Barth, H., Preiss, J. C., Hofmann, F. & Aktories, K. Characterization of the catalytic site of the ADP-ribosyltransferase Clostridium botulinum C2 toxin by site-directed mutagenesis. J. Biol. Chem. 273, 29506-29511 (1998).
57. US20090269361 A1.
58. WO2013126690 A1.

What is claimed is:

1. A composition for delivering an agent to a target cell, comprising
   a target cell binding unit,
   a pore-forming unit,
   a rigid synthetic linker linking the target cell binding unit and the pore-forming unit, and
   a payload unit comprising the agent, wherein said payload unit binds non-covalently to a pore formed by the pore-forming unit upon activation and oligomerization of the pore-forming unit;
   wherein the pore-forming unit is a polypeptide derived from a first AB type of non-neurotoxic binary toxin, and wherein the target cell binding unit is a polypeptide derived from a second AB type of toxin, said second AB type being different from the first AB type, wherein the target cell binding unit binds to a neural cell, and wherein the target cell binding unit and the pore-forming unit are covalently linked through the rigid synthetic linker to form a polypeptide having at least 90% sequence identity to the amino acid sequence of SEQ ID NO: 4.

2. The composition of claim 1, wherein the pore-forming unit is a polypeptide or a polypeptide oligomer derived from the pore-forming unit of *Clostridium botulinum* toxin C2.

3. The composition of claim 1, wherein the composition delivers the agent to a neural cell.

4. The composition of claim 1, wherein the target cell binding unit is a polypeptide or a polypeptide oligomer derived from the binding domain of the heavy chain of *C. botulinum* neurotoxin C1 (C1 Hcc).

5. The composition of claim 1, wherein the agent comprises at least one member selected from the group consisting of a therapeutic agent, a diagnostic agent, and combinations thereof.

6. The composition of claim 1, wherein the agent comprises at least one member selected from the group consisting of a toxin, a cell cycle blocker, an apoptosis inducing agent, an inhibitor of DNA replication, an inhibitor of RNA synthesis, an inhibitor of protein synthesis, an enzyme, a protein binding agent, an antibody, a neutralizing antibody, a labeling agent, magnetic beads, and combinations thereof.

7. The composition of claim 1, wherein the agent comprises an ADP-ribosyltransferase.

8. The composition of claim 1, wherein the agent comprises C2I from *Clostridium botulinum* toxin C2.

9. The composition of claim 1, wherein the agent comprises a fluorescent agent.

10. The composition of claim 1, wherein the target cell binding unit comprises the binding domain of the heavy chain of *C. botulinum* neurotoxin C1 (C1 Hcc), wherein the pore-forming unit comprises the pore-forming domain of *Clostridium botulinum* toxin C-2, and wherein the payload unit comprises C2I from *Clostridium botulinum* toxin C-2.

11. The composition of claim 1, wherein the payload unit comprises a polypeptide having at least 90% sequence identity to amino acid sequence of SEQ ID NO: 6.

12. A method of delivering an agent to a target cell, comprising administering the composition of claim 1 to a target cell.

13. The method of claim 12, wherein the composition is administered to a subject by injection, wherein the subject comprises the target cell.

14. The method of claim 12, wherein the target cell is a member selected from the group consisting of a cell of a brain tumor, a cell of a neuroblastoma, and a cell of a retinoblastoma, peripheral neuron; motor neuron, sensory neuron, and combination thereof.

15. A composition for delivering an agent to a target cell, comprising
a target cell binding unit,
a pore-forming unit,
a rigid synthetic linker linking the target cell binding unit and the pore-forming unit, and
a payload unit comprising the agent, wherein said payload unit binds non-covalently to a pore formed by the pore-forming unit upon activation and oligomerization of the pore-forming unit;
wherein the pore-forming unit is a polypeptide derived from a first AB type of non-neurotoxic binary toxin, and wherein the target cell binding unit is a polypeptide derived from a second AB type of toxin, said second AB type being different from the first AB type, and wherein the target cell binding unit binds to a neural cell; and
wherein the rigid synthetic linker comprises a polypeptide having at least 90% sequence identity to the amino acid sequence set forth in SEQ ID NO: 5.

16. The composition of claim 1, wherein the neural cell is a sensory neuron.

17. A composition for delivering an agent to a target cell, comprising
a target cell binding unit,
a pore-forming unit,
a rigid synthetic linker linking the target cell binding unit and the pore-forming unit, and
a payload unit comprising the agent, wherein said payload unit binds non-covalently to a pore formed by the pore-forming unit upon activation and oligomerization of the pore-forming unit;
wherein the pore-forming unit is a polypeptide derived from a first AB type of non-neurotoxic binary toxin, and wherein the target cell binding unit is a polypeptide derived from a second AB type of toxin, said second AB type being different from the first AB type, wherein the target cell binding unit binds to a neural cell, and
wherein the target cell binding unit comprises a polypeptide having at least 90% sequence identity to the amino acid sequence 230-426 of SEQ ID NO: 1, wherein the pore-forming unit comprises a polypeptide having at least 90% sequence identity to the amino acid sequence 1-591 of SEQ ID NO: 2, and
wherein the rigid synthetic linker comprises a polypeptide having at least 90% sequence identity to the amino acid sequence set forth in SEQ ID NO: 5.

* * * * *

SEQUENCE LISTING

```
<160> NUMBER OF SEQ ID NOS: 14

<210> SEQ ID NO 1
<211> LENGTH: 426
<212> TYPE: PRT
<213> ORGANISM: Clostridium botulinum

<400> SEQUENCE: 1

Asn Asn Ile Asn Asp Ser Lys Ile Leu Ser Leu Gln Asn Arg Lys Asn
1               5                   10                  15

Thr Leu Val Asp Thr Ser Gly Tyr Asn Ala Glu Val Ser Glu Glu Gly
            20                  25                  30

Asp Val Gln Leu Asn Pro Ile Phe Pro Phe Asp Phe Lys Leu Gly Ser
        35                  40                  45

Ser Gly Glu Asp Arg Gly Lys Val Ile Val Thr Gln Asn Glu Asn Ile
    50                  55                  60

Val Tyr Asn Ser Met Tyr Glu Ser Phe Ser Ile Ser Phe Trp Ile Arg
65                  70                  75                  80

Ile Asn Lys Trp Val Ser Asn Leu Pro Gly Tyr Thr Ile Ile Asp Ser
                85                  90                  95

Val Lys Asn Asn Ser Gly Trp Ser Ile Gly Ile Ile Ser Asn Phe Leu
            100                 105                 110

Val Phe Thr Leu Lys Gln Asn Glu Asp Ser Glu Gln Ser Ile Asn Phe
        115                 120                 125

Ser Tyr Asp Ile Ser Asn Asn Ala Pro Gly Tyr Asn Lys Trp Phe Phe
```

```
            130                 135                 140
Val Thr Val Thr Asn Asn Met Met Gly Asn Met Lys Ile Tyr Ile Asn
145                 150                 155                 160

Gly Lys Leu Ile Asp Thr Ile Lys Val Lys Glu Leu Thr Gly Ile Asn
                165                 170                 175

Phe Ser Lys Thr Ile Thr Phe Glu Ile Asn Lys Ile Pro Asp Thr Gly
                180                 185                 190

Leu Ile Thr Ser Asp Ser Asp Asn Ile Asn Met Trp Ile Arg Asp Phe
                195                 200                 205

Tyr Ile Phe Ala Lys Glu Leu Asp Gly Lys Asp Ile Asn Ile Leu Phe
            210                 215                 220

Asn Ser Leu Gln Tyr Thr Asn Val Val Lys Asp Tyr Trp Gly Asn Asp
225                 230                 235                 240

Leu Arg Tyr Asn Lys Glu Tyr Tyr Met Val Asn Ile Asp Tyr Leu Asn
                245                 250                 255

Arg Tyr Met Tyr Ala Asn Ser Arg Gln Ile Val Phe Asn Thr Arg Arg
                260                 265                 270

Asn Asn Asn Asp Phe Asn Glu Gly Tyr Lys Ile Ile Lys Arg Ile
                275                 280                 285

Arg Gly Asn Thr Asn Asp Thr Arg Val Arg Gly Gly Asp Ile Leu Tyr
            290                 295                 300

Phe Asp Met Thr Ile Asn Asn Lys Ala Tyr Asn Leu Phe Met Lys Asn
305                 310                 315                 320

Glu Thr Met Tyr Ala Asp Asn His Ser Thr Glu Asp Ile Tyr Ala Ile
                325                 330                 335

Gly Leu Arg Glu Gln Thr Lys Asp Ile Asn Asp Asn Ile Ile Phe Gln
                340                 345                 350

Ile Gln Pro Met Asn Asn Thr Tyr Tyr Tyr Ala Ser Gln Ile Phe Lys
                355                 360                 365

Ser Asn Phe Asn Gly Glu Asn Ile Ser Gly Ile Cys Ser Ile Gly Thr
                370                 375                 380

Tyr Arg Phe Arg Leu Gly Gly Asp Trp Tyr Arg His Asn Tyr Leu Val
385                 390                 395                 400

Pro Thr Val Lys Gln Gly Asn Tyr Ala Ser Leu Leu Glu Ser Thr Ser
                405                 410                 415

Thr His Trp Gly Phe Val Pro Val Ser Glu
                420                 425

<210> SEQ ID NO 2
<211> LENGTH: 714
<212> TYPE: PRT
<213> ORGANISM: Clostridium botulinum

<400> SEQUENCE: 2

Met Leu Val Ser Lys Phe Glu Asn Ser Val Lys Asn Ser Asn Lys Asn
1               5                   10                  15

Tyr Phe Thr Ile Asn Gly Leu Met Gly Tyr Tyr Phe Glu Asn Asp Phe
                20                  25                  30

Phe Asn Leu Asn Ile Ile Ser Pro Thr Leu Asp Gly Asn Leu Thr Phe
            35                  40                  45

Ser Lys Glu Asp Ile Asn Ser Ile Leu Gly Asn Lys Ile Ile Lys Ser
            50                  55                  60

Ala Arg Trp Ile Gly Leu Ile Lys Pro Ser Ile Thr Gly Glu Tyr Ile
65              70                  75                  80
```

```
Leu Ser Thr Asn Ser Pro Asn Cys Arg Val Glu Leu Asn Gly Glu Ile
                85                  90                  95

Phe Asn Leu Ser Leu Asn Thr Ser Asn Thr Val Asn Leu Ile Gln Gly
            100                 105                 110

Asn Val Tyr Asp Ile Arg Ile Glu Gln Leu Met Ser Glu Asn Gln Leu
        115                 120                 125

Leu Lys Asn Tyr Glu Gly Ile Lys Leu Tyr Trp Glu Thr Ser Asp Ile
    130                 135                 140

Ile Lys Glu Ile Ile Pro Ser Glu Val Leu Leu Lys Pro Asn Tyr Ser
145                 150                 155                 160

Asn Thr Asn Glu Lys Ser Lys Phe Ile Pro Asn Asn Thr Leu Phe Ser
                165                 170                 175

Asn Ala Lys Leu Lys Ala Asn Ala Asn Arg Asp Thr Asp Arg Asp Gly
            180                 185                 190

Ile Pro Asp Glu Trp Glu Ile Asn Gly Tyr Thr Val Met Asn Gln Lys
        195                 200                 205

Ala Val Ala Trp Asp Asp Lys Phe Ala Ala Asn Gly Tyr Lys Lys Tyr
    210                 215                 220

Val Ser Asn Pro Phe Lys Pro Cys Thr Ala Asn Asp Pro Tyr Thr Asp
225                 230                 235                 240

Phe Glu Lys Val Ser Gly Gln Ile Asp Pro Ser Val Ser Met Val Ala
                245                 250                 255

Arg Asp Pro Met Ile Ser Ala Tyr Pro Ile Val Gly Val Gln Met Glu
            260                 265                 270

Arg Leu Val Val Ser Lys Ser Glu Thr Ile Thr Gly Asp Ser Thr Lys
        275                 280                 285

Ser Met Ser Lys Ser Thr Ser His Ser Thr Asn Ile Asn Thr Val
    290                 295                 300

Gly Ala Glu Val Ser Gly Ser Leu Gln Leu Ala Gly Gly Ile Phe Pro
305                 310                 315                 320

Val Phe Ser Met Ser Ala Ser Ala Asn Tyr Ser His Thr Trp Gln Asn
                325                 330                 335

Thr Ser Thr Val Asp Asp Thr Thr Gly Glu Ser Phe Ser Gln Gly Leu
            340                 345                 350

Ser Ile Asn Thr Ala Glu Ser Ala Tyr Ile Asn Pro Asn Ile Arg Tyr
        355                 360                 365

Tyr Asn Thr Gly Thr Ala Pro Val Tyr Asn Val Thr Pro Thr Thr Thr
    370                 375                 380

Ile Val Ile Asp Lys Gln Ser Val Ala Thr Ile Lys Gly Gln Glu Ser
385                 390                 395                 400

Leu Ile Gly Asp Tyr Leu Asn Pro Gly Gly Thr Tyr Pro Ile Ile Gly
                405                 410                 415

Glu Pro Pro Met Ala Leu Asn Thr Met Asp Gln Phe Ser Ser Arg Leu
            420                 425                 430

Ile Pro Ile Asn Tyr Asn Gln Leu Lys Ser Ile Asp Asn Gly Gly Thr
        435                 440                 445

Val Met Leu Ser Thr Ser Gln Phe Thr Gly Asn Phe Ala Lys Tyr Asn
    450                 455                 460

Ser Asn Gly Asn Leu Val Thr Asp Gly Asn Asn Trp Gly Pro Tyr Leu
465                 470                 475                 480

Gly Thr Ile Lys Ser Thr Thr Ala Ser Leu Thr Leu Ser Leu Pro Asp
                485                 490                 495

Gln Thr Thr Gln Val Ala Val Val Ala Pro Asn Phe Ser Asp Pro Glu
```

```
            500                 505                 510
Asp Lys Thr Pro Arg Leu Thr Leu Glu Gln Ala Leu Val Lys Ala Phe
            515                 520                 525

Arg Leu Glu Lys Lys Asn Gly Lys Phe Tyr Phe His Gly Met Glu Ile
            530                 535                 540

Ser Ala Asn Gln Lys Ile Gln Val Phe Leu Asp Arg Asn Thr Asn Val
545                 550                 555                 560

Asp Phe Glu Asn Gln Leu Lys Asn Thr Ala Asn Lys Asp Ile Met Asn
                565                 570                 575

Cys Ile Ile Lys Arg Asn Met Asn Ile Leu Val Lys Val Ile Thr Phe
                580                 585                 590

Lys Glu Asn Ile Ser Ser Ile Asn Ile Ile Asn Asp Thr Asn Phe Gly
                595                 600                 605

Val Glu Ser Met Thr Gly Leu Ser Lys Arg Ile Lys Gly Asn Asp Gly
            610                 615                 620

Ile Tyr Arg Ala Ser Thr Lys Ser Phe Ser Phe Lys Ser Lys Glu Ile
625                 630                 635                 640

Lys Tyr Pro Glu Gly Phe Tyr Arg Met Arg Phe Val Ile Gln Ser Tyr
                645                 650                 655

Glu Pro Phe Thr Cys Asn Phe Lys Leu Phe Asn Asn Leu Ile Tyr Ser
                660                 665                 670

Asn Ser Phe Asp Ile Gly Tyr Tyr Asp Glu Phe Tyr Phe Tyr Cys
            675                 680                 685

Asn Gly Ser Lys Ser Phe Phe Asp Ile Ser Cys Asp Ile Ile Asn Ser
            690                 695                 700

Ile Asn Arg Leu Ser Gly Val Phe Leu Ile
705                 710

<210> SEQ ID NO 3
<211> LENGTH: 431
<212> TYPE: PRT
<213> ORGANISM: Clostridium botulinum

<400> SEQUENCE: 3

Met Pro Ile Ile Lys Glu Pro Ile Asp Phe Ile Asn Lys Pro Glu Ser
1               5                   10                  15

Glu Ala Lys Glu Trp Gly Lys Glu Glu Lys Arg Trp Phe Thr Lys
            20                  25                  30

Leu Asn Asn Leu Glu Glu Val Ala Val Asn Gln Leu Lys Asn Lys Glu
            35                  40                  45

Tyr Lys Thr Lys Ile Asp Asn Phe Ser Thr Asp Ile Leu Phe Ser Ser
50                  55                  60

Leu Thr Ala Ile Glu Ile Met Lys Glu Asp Glu Asn Gln Asn Leu Phe
65                  70                  75                  80

Asp Val Glu Arg Ile Arg Glu Ala Leu Leu Lys Asn Thr Leu Asp Arg
                85                  90                  95

Asp Ala Ile Gly Tyr Val Asn Phe Thr Pro Lys Glu Leu Gly Ile Asn
            100                 105                 110

Phe Ser Ile Arg Asp Val Glu Leu Asp Arg Asp Ile Ser Asp Glu Thr
            115                 120                 125

Leu Asp Lys Val Arg Gln Gln Ile Ile Asn Gln Glu Tyr Thr Lys Phe
            130                 135                 140

Ser Phe Ile Ser Leu Gly Leu Asn Asp Asn Ser Ile Asn Glu Ser Val
145                 150                 155                 160
```

```
Pro Val Ile Val Lys Thr Arg Val Pro Thr Thr Phe Asp Tyr Gly Val
            165                 170                 175

Leu Asn Asp Lys Glu Thr Val Ser Leu Leu Asn Gln Gly Phe Ser
        180                 185                 190

Ile Ile Pro Glu Ser Ala Ile Ile Thr Thr Ile Lys Gly Lys Asp Tyr
        195                 200                 205

Ile Leu Ile Glu Gly Ser Leu Ser Gln Glu Leu Asp Phe Tyr Asn Lys
        210                 215                 220

Gly Ser Glu Ala Trp Gly Ala Glu Asn Tyr Gly Asp Tyr Ile Ser Lys
225                 230                 235                 240

Leu Ser His Glu Gln Leu Gly Ala Leu Glu Gly Tyr Leu His Ser Asp
            245                 250                 255

Tyr Lys Ala Ile Asn Ser Tyr Leu Arg Asn Asn Arg Val Pro Asn Asn
        260                 265                 270

Asp Glu Leu Asn Lys Lys Ile Glu Leu Ile Ser Ser Ala Leu Ser Val
        275                 280                 285

Lys Pro Ile Pro Gln Thr Leu Ile Ala Tyr Arg Arg Val Asp Gly Ile
        290                 295                 300

Pro Phe Asp Leu Pro Ser Asp Phe Ser Phe Asp Lys Lys Glu Asn Gly
305                 310                 315                 320

Glu Ile Ile Ala Asp Lys Gln Lys Leu Asn Glu Phe Ile Asp Lys Trp
            325                 330                 335

Thr Gly Lys Glu Ile Glu Asn Leu Ser Phe Ser Ser Thr Ser Leu Lys
        340                 345                 350

Ser Thr Pro Ser Ser Phe Ser Lys Ser Arg Phe Ile Phe Arg Leu Arg
        355                 360                 365

Leu Ser Glu Gly Ala Ile Gly Ala Phe Ile Tyr Gly Phe Ser Gly Phe
        370                 375                 380

Gln Asp Glu Gln Glu Ile Leu Leu Asn Lys Asn Ser Thr Phe Lys Ile
385                 390                 395                 400

Phe Arg Ile Thr Pro Ile Thr Ser Ile Ile Asn Arg Val Thr Lys Met
            405                 410                 415

Thr Gln Val Val Ile Asp Ala Glu Gly Ile Gln Asn Lys Glu Ile
        420                 425                 430

<210> SEQ ID NO 4
<211> LENGTH: 812
<212> TYPE: PRT
<213> ORGANISM: Clostridium botulinum

<400> SEQUENCE: 4

Met Leu Val Ser Lys Phe Glu Asn Ser Val Lys Asn Ser Asn Lys Asn
1               5                   10                  15

Tyr Phe Thr Ile Asn Gly Leu Met Gly Tyr Tyr Phe Glu Asn Asp Phe
            20                  25                  30

Phe Asn Leu Asn Ile Ile Ser Pro Thr Leu Asp Gly Asn Leu Thr Phe
        35                  40                  45

Ser Lys Glu Asp Ile Asn Ser Ile Leu Gly Asn Lys Ile Ile Lys Ser
    50                  55                  60

Ala Arg Trp Ile Gly Leu Ile Lys Pro Ser Ile Thr Gly Glu Tyr Ile
65                  70                  75                  80

Leu Ser Thr Asn Ser Pro Asn Cys Arg Val Glu Leu Asn Gly Glu Ile
            85                  90                  95

Phe Asn Leu Ser Leu Asn Thr Ser Asn Thr Val Asn Leu Ile Gln Gly
            100                 105                 110
```

```
Asn Val Tyr Asp Ile Arg Ile Glu Gln Leu Met Ser Glu Asn Gln Leu
        115                 120                 125

Leu Lys Asn Tyr Glu Gly Ile Lys Leu Tyr Trp Glu Thr Ser Asp Ile
        130                 135                 140

Ile Lys Glu Ile Ile Pro Ser Glu Val Leu Leu Lys Pro Asn Tyr Ser
145                 150                 155                 160

Asn Thr Asn Glu Lys Ser Lys Phe Ile Pro Asn Asn Thr Leu Phe Ser
                165                 170                 175

Asn Ala Lys Leu Lys Ala Asn Ala Asn Arg Asp Thr Asp Arg Asp Gly
                180                 185                 190

Ile Pro Asp Glu Trp Glu Ile Asn Gly Tyr Thr Val Met Asn Gln Lys
            195                 200                 205

Ala Val Ala Trp Asp Asp Lys Phe Ala Ala Asn Gly Tyr Lys Lys Tyr
        210                 215                 220

Val Ser Asn Pro Phe Lys Pro Cys Thr Ala Asn Asp Pro Tyr Thr Asp
225                 230                 235                 240

Phe Glu Lys Val Ser Gly Gln Ile Asp Pro Ser Val Ser Met Val Ala
                245                 250                 255

Arg Asp Pro Met Ile Ser Ala Tyr Pro Ile Val Gly Val Gln Met Glu
            260                 265                 270

Arg Leu Val Val Ser Lys Ser Glu Thr Ile Thr Gly Asp Ser Thr Lys
        275                 280                 285

Ser Met Ser Lys Ser Thr Ser His Ser Ser Thr Asn Ile Asn Thr Val
        290                 295                 300

Gly Ala Glu Val Ser Gly Ser Leu Gln Leu Ala Gly Gly Ile Phe Pro
305                 310                 315                 320

Val Phe Ser Met Ser Ala Ser Ala Asn Tyr Ser His Thr Trp Gln Asn
                325                 330                 335

Thr Ser Thr Val Asp Asp Thr Thr Gly Glu Ser Phe Ser Gln Gly Leu
            340                 345                 350

Ser Ile Asn Thr Ala Glu Ser Ala Tyr Ile Asn Pro Asn Ile Arg Tyr
        355                 360                 365

Tyr Asn Thr Gly Thr Ala Pro Val Tyr Asn Val Thr Pro Thr Thr Thr
        370                 375                 380

Ile Val Ile Asp Lys Gln Ser Val Ala Thr Ile Lys Gly Gln Glu Ser
385                 390                 395                 400

Leu Ile Gly Asp Tyr Leu Asn Pro Gly Gly Thr Tyr Pro Ile Ile Gly
                405                 410                 415

Glu Pro Pro Met Ala Leu Asn Thr Met Asp Gln Phe Ser Ser Arg Leu
            420                 425                 430

Ile Pro Ile Asn Tyr Asn Gln Leu Lys Ser Ile Asp Asn Gly Gly Thr
        435                 440                 445

Val Met Leu Ser Thr Ser Gln Phe Thr Gly Asn Phe Ala Lys Tyr Asn
        450                 455                 460

Ser Asn Gly Asn Leu Val Thr Asp Gly Asn Asn Trp Gly Pro Tyr Leu
465                 470                 475                 480

Gly Thr Ile Lys Ser Thr Thr Ala Ser Leu Thr Leu Ser Leu Pro Asp
                485                 490                 495

Gln Thr Thr Gln Val Ala Val Ala Pro Asn Phe Ser Asp Pro Glu
            500                 505                 510

Asp Lys Thr Pro Arg Leu Thr Leu Glu Gln Ala Leu Val Lys Ala Phe
        515                 520                 525
```

-continued

```
Arg Leu Glu Lys Lys Asn Gly Lys Phe Tyr Phe His Gly Met Glu Ile
    530                 535                 540

Ser Ala Asn Gln Lys Ile Gln Val Phe Leu Asp Arg Asn Thr Asn Val
545                 550                 555                 560

Asp Phe Glu Asn Gln Leu Lys Asn Thr Ala Asn Lys Asp Ile Met Asn
                565                 570                 575

Cys Ile Ile Lys Arg Asn Met Asn Ile Leu Val Lys Val Ile Thr Gly
                580                 585                 590

Ser Glu Pro Glu Pro Glu Pro Glu Pro Glu Pro Glu Pro Glu Pro Glu
            595                 600                 605

Pro Glu Pro Glu Pro Gly Ser Thr Asn Val Val Lys Asp Tyr Trp Gly
610                 615                 620

Asn Asp Leu Arg Tyr Asn Lys Glu Tyr Tyr Met Val Asn Ile Asp Tyr
625                 630                 635                 640

Leu Asn Arg Tyr Met Tyr Ala Asn Ser Arg Gln Ile Val Phe Asn Thr
                645                 650                 655

Arg Arg Asn Asn Asn Asp Phe Asn Glu Gly Tyr Lys Ile Ile Ile Lys
                660                 665                 670

Arg Ile Arg Gly Asn Thr Asn Asp Thr Arg Val Arg Gly Gly Asp Ile
                675                 680                 685

Leu Tyr Phe Asp Met Thr Ile Asn Asn Lys Ala Tyr Asn Leu Phe Met
690                 695                 700

Lys Asn Glu Thr Met Tyr Ala Asp Asn His Ser Thr Glu Asp Ile Tyr
705                 710                 715                 720

Ala Ile Gly Leu Arg Glu Gln Thr Lys Asp Ile Asn Asp Asn Ile Ile
                725                 730                 735

Phe Gln Ile Gln Pro Met Asn Asn Thr Tyr Tyr Tyr Ala Ser Gln Ile
                740                 745                 750

Phe Lys Ser Asn Phe Asn Gly Glu Asn Ile Ser Gly Ile Cys Ser Ile
            755                 760                 765

Gly Thr Tyr Arg Phe Arg Leu Gly Gly Asp Trp Tyr Arg His Asn Tyr
770                 775                 780

Leu Val Pro Thr Val Lys Gln Gly Asn Tyr Ala Ser Leu Leu Glu Ser
785                 790                 795                 800

Thr Ser Thr His Trp Gly Phe Val Pro Val Ser Glu
                805                 810

<210> SEQ ID NO 5
<211> LENGTH: 24
<212> TYPE: PRT
<213> ORGANISM: Artificial Sequence
<220> FEATURE:
<223> OTHER INFORMATION: Synthetic

<400> SEQUENCE: 5

Gly Ser Glu Pro Glu Pro Glu Pro Glu Pro Glu Pro Glu Pro Glu Pro
1               5                   10                  15

Glu Pro Glu Pro Glu Pro Gly Ser
            20

<210> SEQ ID NO 6
<211> LENGTH: 225
<212> TYPE: PRT
<213> ORGANISM: Clostridium botulinum

<400> SEQUENCE: 6

Met Pro Ile Ile Lys Glu Pro Ile Asp Phe Ile Asn Lys Pro Glu Ser
```

```
  1               5                   10                  15
Glu Ala Lys Glu Trp Gly Lys Glu Glu Lys Arg Trp Phe Thr Lys
              20                  25                  30
Leu Asn Asn Leu Glu Glu Val Ala Val Asn Gln Leu Lys Asn Lys Glu
              35                  40                  45
Tyr Lys Thr Lys Ile Asp Asn Phe Ser Thr Asp Ile Leu Phe Ser Ser
     50                  55                  60
Leu Thr Ala Ile Glu Ile Met Lys Glu Asp Gly Asn Gln Asn Leu Phe
65                  70                  75                  80
Asp Val Glu Arg Ile Arg Glu Ala Leu Leu Lys Asn Thr Leu Asp Arg
                 85                  90                  95
Asp Ala Ile Gly Tyr Val Asn Phe Thr Pro Lys Glu Leu Gly Ile Asn
              100                 105                 110
Phe Ser Ile Arg Asp Val Glu Leu Asp Arg Asp Ile Ser Asp Glu Thr
              115                 120                 125
Leu Asp Lys Val Arg Gln Gln Ile Ile Asn Gln Glu Tyr Thr Lys Phe
     130                 135                 140
Ser Phe Ile Ser Leu Gly Leu Asn Asp Asn Ser Ile Asn Glu Ser Val
145                 150                 155                 160
Pro Val Ile Val Lys Thr Arg Val Pro Thr Thr Phe Asp Tyr Gly Val
                 165                 170                 175
Leu Asn Asp Lys Glu Thr Val Ser Leu Leu Asn Gln Gly Phe Ser
              180                 185                 190
Ile Ile Pro Glu Ser Ala Ile Ile Thr Thr Ile Lys Gly Lys Asp Tyr
              195                 200                 205
Ile Leu Ile Glu Gly Ser Leu Ser Gln Glu Leu Asp Phe Tyr Asn Lys
     210                 215                 220
Gly
225

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
cgcggatcca tgctggtctc c                                              21

<210> SEQ ID NO 8
<211> LENGTH: 53
<212> TYPE: DNA
<213> ORGANISM: Artificial Sequence
<220> FEATURE:
<223> OTHER INFORMATION: synthetic

<400> SEQUENCE: 8
ccggctctgg ttccggttca gaaccggtga tcactttgac cagaatattc atg          53

<210> SEQ ID NO 9
<211> LENGTH: 53
<212> TYPE: DNA
<213> ORGANISM: Artificial Sequence
<220> FEATURE:
<223> OTHER INFORMATION: synthetic

<400> SEQUENCE: 9
ccagaaccag agccagaacc aggttctacc aacgttgtca agactattg ggg            53
```

```
<210> SEQ ID NO 10
<211> LENGTH: 27
<212> TYPE: DNA
<213> ORGANISM: Artificial Sequence
<220> FEATURE:
<223> OTHER INFORMATION: synthetic

<400> SEQUENCE: 10
cgggaattct tattctgaaa ccgggac                                        27

<210> SEQ ID NO 11
<211> LENGTH: 58
<212> TYPE: DNA
<213> ORGANISM: Artificial Sequence
<220> FEATURE:
<223> OTHER INFORMATION: synthetic

<400> SEQUENCE: 11
aaccggaacc agagccggaa ccggaaccgg aaccggagcc agaaccagag ccagaacc      58

<210> SEQ ID NO 12
<211> LENGTH: 39
<212> TYPE: DNA
<213> ORGANISM: Artificial Sequence
<220> FEATURE:
<223> OTHER INFORMATION: synthetic

<400> SEQUENCE: 12
cgcggatcca tgggcaccaa cgttgtcaaa gactattgg                           39

<210> SEQ ID NO 13
<211> LENGTH: 30
<212> TYPE: DNA
<213> ORGANISM: Artificial Sequence
<220> FEATURE:
<223> OTHER INFORMATION: synthetic

<400> SEQUENCE: 13
cgggaattct taggtgatca ctttgaccag                                     30

<210> SEQ ID NO 14
<211> LENGTH: 52
<212> TYPE: DNA
<213> ORGANISM: Artificial Sequence
<220> FEATURE:
<223> OTHER INFORMATION: synthetic

<400> SEQUENCE: 14
cgcggatcca tgccgattat taaagaaccg attgacttca tcaacaaacc gg            52
```